(12) United States Patent
Liu et al.

(10) Patent No.: US 8,288,431 B2
(45) Date of Patent: Oct. 16, 2012

(54) SUBSTITUTED SPIROINDOLINONES

(75) Inventors: Jin-Jun Liu, Warren Township, NJ (US); Jing Zhang, Parsippany, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 37 days.

(21) Appl. No.: 13/009,225

(22) Filed: Jan. 19, 2011

(65) Prior Publication Data
US 2011/0201635 A1  Aug. 18, 2011

Related U.S. Application Data

(60) Provisional application No. 61/305,352, filed on Feb. 17, 2010.

(51) Int. Cl.
*A61K 31/4015* (2006.01)
*C07D 487/10* (2006.01)
(52) U.S. Cl. .................... 514/409; 548/409; 548/410
(58) Field of Classification Search .............. 548/409, 548/410; 514/409
See application file for complete search history.

(56) References Cited

U.S. PATENT DOCUMENTS

| | | | |
|---|---|---|---|
| 2,759,935 A | 8/1956 | Speeter | |
| 3,441,570 A | 4/1969 | Meyer | |
| 3,686,210 A | 8/1972 | Bell | |
| 4,020,179 A | 4/1977 | Irvine | |
| 6,511,974 B1 | 1/2003 | Dusza et al. | |
| 6,774,132 B1 | 8/2004 | Claesson et al. | |
| 7,495,007 B2* | 2/2009 | Chen et al. | 514/278 |
| 7,553,833 B2 | 6/2009 | Liu et al. | |
| 7,638,548 B2 | 12/2009 | Liu et al. | |
| 7,737,174 B2* | 6/2010 | Wang et al. | 514/421 |
| 7,759,383 B2* | 7/2010 | Wang et al. | 514/409 |
| 8,088,815 B2* | 1/2012 | Bartkovitz et al. | 514/409 |
| 8,088,931 B2* | 1/2012 | Wang et al. | 548/409 |
| 8,134,001 B2* | 3/2012 | Ding et al. | 546/17 |
| 2007/0213341 A1 | 9/2007 | Chen et al. | |
| 2008/0009486 A1 | 1/2008 | Chen et al. | |
| 2008/0114013 A1 | 5/2008 | Liu et al. | |

FOREIGN PATENT DOCUMENTS

| | | |
|---|---|---|
| EP | 0288847 | 4/1988 |
| EP | 0947511 | 10/1999 |
| JP | 55 129284 | 6/1980 |
| JP | 2000191661 | 7/2000 |
| WO | 97/15556 | 5/1997 |
| WO | 98/02432 | 1/1998 |
| WO | 98/54167 | 12/1998 |
| WO | 00/15657 | 3/2000 |
| WO | 00/71129 | 11/2000 |
| WO | 01/05790 | 1/2001 |
| WO | 03/008407 | 1/2003 |
| WO | 03/078394 | 9/2003 |
| WO | 2006/080574 | 8/2006 |
| WO | 2006/091646 | 8/2006 |
| WO | 2006091646 | 8/2006 |
| WO | 2006/136606 | 12/2006 |
| WO | 2007104664 | 9/2007 |
| WO | 2007104714 | 9/2007 |
| WO | 2008/036168 | 3/2008 |
| WO | 2008036168 | 3/2008 |
| WO | 2008/055812 | 5/2008 |
| WO | 2008080822 | 7/2008 |
| WO | 2008005268 | 10/2008 |
| WO | 2009080488 | 7/2009 |

OTHER PUBLICATIONS

Simplicio, Ana, Molecules 2008. 519-547.
Sairim, Carbohydrate Research 338_2003_303-306.
Sun, Cancer Biology & Therapy (2008) 7 (6), 845-852.
Ding Ke et al: Journal of Medicinal Chemistry 49:12 (2006) 3432-3435 XP002496820.
International Search Report for PCT/EP2011/052083 dated Apr. 20, 2011.
Ansel et al., Pharmaceutical Dosage Forms and Drug Delivery Systems (6th Ed. 1995) at pp. 196.
Ansel et al., Pharmaceutical Dosage Forms and Drug Delivery Systems (6th Ed. 1995) at p. 456-457.
Kraynack, E. A.; Dalgard, J. E.; Gaeta, F. C. A. Tetrahedron Letters, 1998, 39, 7679-7682.
P. Erway, et al., J. Med. Chem. 2002, 45, 1487-1499.
Elliott, I. W.; Rivers, P. J. Org. Chem. 1964, 29, 2438-2440.
Andreani, A.; et al., Eur. J. Med. Chem. 1990, 25, 187-190.
Christopher Hulme, et al., Bioorganic & Medicinal Chemistry Letters, vol. 8, pp. 175-178 (1998), XP002405133.
F.D. Dopp, et al., J. Heterocyclic Chem., vol. 17, No. 9, pp. 1329-1330 (1980), XP002405134.
Gordon N. Walker, et al., J. Med. Chem., vol. 8, pp. 626-637 (1965), XP002405135.
Stanislav Kafka, et al., J. Org. Chem., vol. 66, pp. 6394-6399 (2001), XP002405136.
Amarnath Natarajan, et al., J. Med. Chem., vol. 47, pp. 1882-1885 (2004), XP002405137.
James C. Powers, J. Org. Chem., vol. 30, pp. 2534-2540 (1965), XP002405138.
Sengodagounder Muthusamy, et al., Synlett, vol. 2002, No. 11, pp. 1783-1786 (2002), XP002405139.

(Continued)

*Primary Examiner* — Golam M M Shameem
(74) *Attorney, Agent, or Firm* — George W. Johnston; Patricia S. Rocha-Tramaloni

(57) ABSTRACT

There is provided a compound of the formula

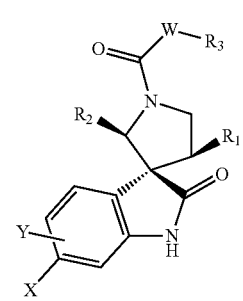

wherein
X, Y, W, $R_1$, $R_2$ and $R_3$ are as described herein. The compounds have activity as anticancer agents.

9 Claims, No Drawings

OTHER PUBLICATIONS

Ward C. Sumpter, J. Am. Chem Soc., vol. 54, pp. 2917-2918 (1932), XP002405141.
H.E. Zaugg, et al., J. Am. Chem. Soc., vol. 84, pp. 4574-4578 (1962), XP002418406.
Steven P. Govek, et al., J. Am. Chem. Soc., vol. 123, pp. 9468-9469 (2001), XP002418407.
Rita Kapiller-Dezofi, et al., New J. Chem., vol. 28, pp. 1214-1220 (2004), XP002418408.
David W. Robertson, et al., J. Med. Chem., vol. 29, pp. 1832-1840 (1986), XP002418409.
Kazuo Takayama, et al., Tetrahedron Letters, vol. 5, pp. 365-368 (1973), XP002418410.
Audris Huang, et al., J. Am. Chem. Soc., vol. 126, pp. 14043-14053 (2004), XP002418411.
Masaru Ogata, et al., Eur. J. Med. Chem.—Chimica Therapeutica, vol. 16, No. 4, pp. 373-379 (1981), XP00907847.
Istvan Moldvai, et al., Arch. Pharm. Pharm. Med. Chem., vol. 329, pp. 541-549 (1996), XP009078456.
Hossein Pajouheish, et al., J. Pharm. Sci., vol. 72, No. 3, pp. 318-321 (1983), XP009078411.
Krishna C. Joshi, et al., Journal of Fluorine Chemistry, vol. 44, pp. 59-72 (1989), XP002418412.
Piyasena Hewawasam, et al., Bioorganic & Medicinal Chemistry Letters, vol. 12, pp. 1023-1026 (2002), XP002418413.
Santiago Barroso, et al., J. Org., Chem., vol. 69, pp. 6821-6829 (2004), XP002418416.
Paul Aeberli, et al., J. Org. Chem., vol. 33, No. 4 pp. 1640-1643 (1968), XP002418417.
A. Walser, et al., J. Org. Chem., vol. 38, No. 3, pp. 449-456 (1973), XP002418418.
Javad Azizian, et al., Synthesis, vol. 2005, No. 7, pp. 1095-1098 (2005), XP 002418427.
Andrew Fensome, et al., Bioorganic & Medicinal Chemistry Letters, vol. 12, pp. 3487-3490 (2002), XP002418428.
T.V. Rajanbabu, et al., J. Org. Chem., vol. 51, pp. 1704-1712 (1986), XP002418429.
Karnail S. Atwal, et al., J. Med. Chem., vol. 39, pp. 304-313 (1996), XP002418430.
Balazs Volk, et al., Eur. J. Org. Chem., pp. 3991-3996 (2003), XP002418431.
Keith Smith, et al., J. Chem. Soc. Perkin Trans. 1, vol. 1999, pp. 2299-2303 (1999), XP002418432.
R.L. Hinman, et al., J. Org. Chem., vol. 29, pp. 2431-2437 (1964), XP002418433.
J. Amer. Chem. Soc (2005) 127 p. 10130.
Hellmann, H. et al, Chemische Berichte, ISSN:009-2440, vol. 86, 1346-1361 (1953) XP002481520.
Alarcon-Vargas, D et al, Carcinogenesis, 23(4):541-547 (2002) XP002481521.
Lippa,Blaise, Bioorganic & Medicinal Chemistry Letters 18, (2008) 3359-3363.
Ding, Journal of Medicinal Chemistry (2006), 49(12), 3432-3435.
Chosez, L., Tetrahedron, (1995) 11021-11042.
Ashimori A. Journal of Organic Chem 57: 17 (2002) 4571-4572 XP002527583.
Ashimori A. Journal of American Chem Society 120 (1998) 6477-6477-6487 XP001038246.
Johnson R.S., Journal of American Chem Society (1900) 796-800 xp002156747.
Ding, Tetrahedron Letters (2005), 46 (35), 5949-5951SUN.
Shangary, Molecular Cancer Therapeutics (2008), 7(6) 1533-1542.
Shangary, Proceedings of National Academy of Science (2008) 105(10) 3933-3938.
Saddler, Blood (2008), 111(3), 1584-1593.

* cited by examiner

US 8,288,431 B2

SUBSTITUTED SPIROINDOLINONES

PRIORITY TO RELATED APPLICATION(S)

This application claims the benefit of U.S. Provisional Application No. 61/305,352, filed Feb. 17, 2010, which is hereby incorporated by reference in its entirety.

SUMMARY OF THE INVENTION

The present invention relates to substituted spiroindolinone derivatives I which act as antagonists of mdm2 interactions and hence are useful as potent and selective anticancer agents. The present compounds are of the general formula

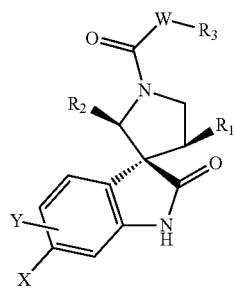

I wherein X, Y, W, $R_1$, $R_2$, and $R_3$ are as described herein and enantiomers and pharmaceutically acceptable salts thereof.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

DETAILED DESCRIPTION OF THE INVENTION

There are provided compounds of the formula

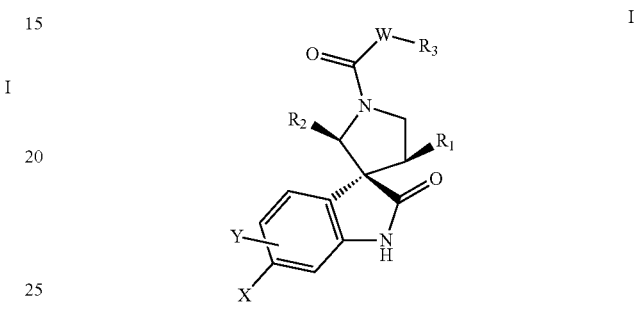

I wherein

X is selected from the group consisting of F, Cl and Br;

Y is a mono substituting group selected from H or F;

$R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_2$ is selected from the group consisting of aryl, substituted aryl, heteroaryl and substituted heteroaryl;

W is NH, O or none;

$R_3$ is selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR'R" and $(CH_2)_n$—SO$_2$NR'R";

n is 0, 1, 2 or 3;

R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle or substituted heterocycle and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle;

and enantiomers and the pharmaceutically acceptable salts thereof.

Preferred are compounds of formula I in which $R_2$ is selected from the group consisting of a substituted phenyl as shown in formula II:

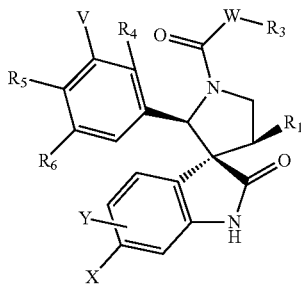

wherein,
X is selected from the group consisting of F, Cl and Br;
Y is a mono substituting group selected from H or F;
V is selected from the group consisting of F, Cl and Br;
$R_4, R_5, R_6$ is selected from H or F with the proviso that at least two of $R_3, R_4, R_5$ are hydrogen;
$R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl;
W is NH, O or none;
$R_3$ is selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR'R" and $(CH_2)_n$—SO$_2$NR'R";
n is 0, 1, 2 or 3;
R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle
and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle;
and enantiomers and the pharmaceutically acceptable salts thereof.

Further preferred are compounds of formula II in which $R_1$ is selected from a group consisting of a substituted lower alkyl shown as formula III:

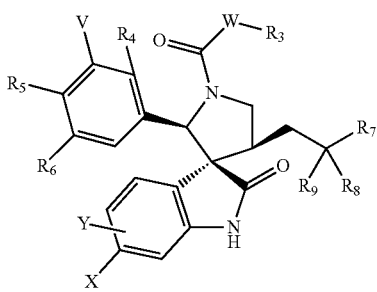

wherein,
X is selected from the group consisting of F, Cl and Br;
Y is a mono substituting group selected from H or F;
V is selected from the group consisting of F, Cl and Br;
$R_4, R_5, R_6$ is selected from H or F with the proviso that at least two of $R_3, R_4, R_5$ are hydrogen;
$R_7, R_8$ are both methyl, or linked to form a cyclopropyl, cyclobutyl, cyclopentyl or cyclohexyl group;
$R_9$ is $(CH_2)_q$—$R_{10}$;
$R_{10}$ is selected from hydrogen, hydroxyl, lower alkyl, lower alkoxy, lower cycloalkenyl, substituted cycloalkenyl, lower cycloalkyl, substituted cycloalkyl, aryl, substituted aryl, hetereoaryl, substituted heteroaryl, hetereocycle or substituted heterocycle;
q is 0, 1 or 2;
W is NH, O or none;
$R_3$ is selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR'R" and $(CH_2)_n$—SO$_2$NR'R";
n is 0, 1, 2 or 3;
R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle
and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle;
and enantiomers and the pharmaceutically acceptable salts thereof.

Most preferred are compounds of formula III in which $R_7$, $R_8$, $R_9$ are methyl as shown in formula IV,

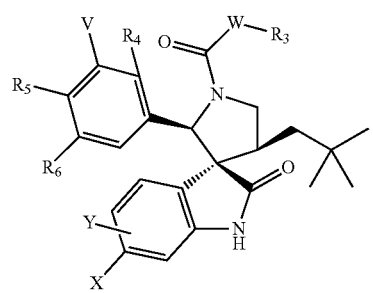

wherein,
X is selected from the group consisting of F, Cl and Br;
Y is a mono substituting group selected from H or F;
V is selected from the group consisting of F, Cl and Br;
$R_4, R_5, R_6$ is selected from H or F with the proviso that at least two of $R_3, R_4, R_5$ are hydrogen;
W is NH or O;
$R_3$ is selected from the group consisting of $(CH_2)_n$—R';
n is 0 or 1;
R' is selected from the group consisting of aryl, substituted aryl, heteroaryl and substituted heteroaryl;
and the pharmaceutically acceptable salts thereof.

Especially preferred are compounds of the formula:
rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide, chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide, rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid ethyl ester, rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid methyl ester, rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid, chiral 4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid, rac-(2'R,3'S,4'S)-6-chloro-2'-(3-chloro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide, rac-4-{[(2'R,3'S,4'S)-6-chloro-2'-(3-chloro-phenyl)-4'-(2,2-dimethyl-propyl)-2-oxo-1,2-dihydro-spiro[indole-3,3'-pyrrolidin]e-1'-carbonyl]-amino}-benzoic acid methyl ester, rac-4-{[(2'R,3'S,4'S)-6-chloro-2'-(3-chloro-phenyl)-4'-(2,2-dimethyl-propyl)-2-oxo-1,2-dihydro-spiro[indole-3,3'-pyrrolidin]e-1'-carbonyl]-amino}-benzoic acid, rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid methyl ester, rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid, chiral 4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid, rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]amino}-piperidine-1-carboxylic acid tert-butyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid piperidin-4-ylamide trifluoroacetic acid, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-yl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide, chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide, rac-(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidine]-1'-carboxylic acid ((S)-3,4-dihydroxy-butyl)-amide, rac-4-({[(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidin]e-1'-carbonyl]-amino}-methyl)-benzoic acid methyl ester, rac-4-({[(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidin]e-1'-carbonyl]-amino}-methyl)-benzoic acid, rac-(2'S,3'S,4'S)-6-chloro-2'-(3-chloro-2-fluoro-phenyl)-4'-(4-hydroxy-2,2-dimethyl-butyl)-2-oxo-1,2-dihydro-spiro[indole-3,3'-pyrrolidine]-1'-carboxylic acid ((S)-3,4-dihydroxy-butyl)-amide, rac-4-{[(2'S,3'S,4'S)-6-chloro-2'-(3-chloro-2-fluoro-phenyl)-4'-(4-hydroxy-2,2-dimethyl-butyl)-2-oxo-1,2-dihydro-spiro[indole-3,3'-pyrrolidin]e-1'-carbonyl]amino}-benzoic acid, rac-4-({[(2'S,3'S,4'S)-6-chloro-2'-(3-chloro-2-fluoro-phenyl)-4'-(2,2-dimethyl-propyl)-2-oxo-1,2-dihydro-spiro[indol e-3,3'-pyrrolidin]e-1'-carbonyl]-amino}-methyl)-piperidine-1-carboxylic acid tert-butyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylmethyl)-amide trifluoroacetic acid, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide, chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-benzyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carboxy-benzyl ester, rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-ethyl)-piperidine-1-carboxylic acid tert-butyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylethyl)-amide trifluoroacetic acid, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-ylethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylethyl)-amide, rac-(2'S,3'S,4'S)-6-chloro-2'-(3-chloro-2-fluoro-phenyl)-4'-(2,2-dimethyl-propyl)-1'-[4-(3-methanesulfonyl-propyl)-piperazine-1-carbonyl]-1H-spiro[indole-3,3'-pyrrolidin]-2-one, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1H-pyrazol-3-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methyl-1H-pyrazol-3-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1,3-dimethyl-1H-pyrazol-4-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (4-nitro-phenyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-phenyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carboxy-phenyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (4-carbamoyl-phenyl)-amide and chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carbamoyl-benzylamide.

Terms & Definitions

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfonyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, hydroxycarbonyl, carboxy, carbamoyl, aminocarbonyl, carboxy lower alkoxy, oxo and CN. Preferred substituents for alkyl are alkoxy and N(lower alkyl)$_2$.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butyryl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl. Where the aryl group is bicyclic a preferred group is 1,3-dioxo-2,3-dihydro-1H-isoindol-5-yl group.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole substituted or unsubstituted triazolyl and substituted or unsubstituted tetrazolyl.

In the case of aryl or heteroaryl which are bicyclic it should be understood that one ring may be aryl while the other is heteroaryl and both being substituted or unsubstituted.

"Heterocycle" or "heterocyclic ring" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like which in turn can be substituted. "Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I-IV as well as their salts that have at least one asymmetric carbon atom may be present as racemic mixtures or different stereoisomers. The various isomers can be isolated by known separation methods, e.g., chromatography.

Compounds disclosed herein and covered by formula I-IV above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

The compounds of the present invention are useful in the treatment or control of cell proliferative disorders, in particular oncological disorders. These compounds and formulations containing said compounds may be particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration; it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"IC50" refers to the concentration of a particular compound required to inhibit 50% of a specific measured activity. $IC_{50}$ can be measured, inter alia, as is described subsequently.

Synthetic Methods

The present invention provides methods for the synthesis of N-substituted spiroindolinone derivatives in formula I. The compounds of the invention can be prepared by processes known in the art. Suitable processes for synthesizing these compounds are provided in the examples.

The starting materials are either commercially available or can be synthesized by methods known to those of ordinary skill in the art. Preparations of intermediates II, III and IV are illustrated in Scheme 1 and 2. In general an appropriately selected aldehyde can be reacted with C-trimethylsilanyl-methylamine in $CH_2Cl_2$ to generate imines II and were used as crude products without purification (Scheme 1).

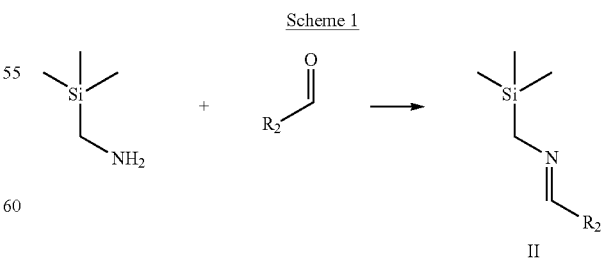

Reagents and conditions:
$CH_2Cl_2$, room temperature, 3 h

Intermediate III can be made from a base-catalyzed condensation reaction of appropriately selected substituted 2-oxindole and aryl or alkyl aldehyde in methanol. The choice of bases includes but is not limited to pyrrolidine or piperidine. The reaction generates III as a mixture of Z- and E-isomers with E-isomer as the major product. Intermediate III can be reacted with di-tert-butyl dicarbonate and a catalytic amount of -(dimethylamine)pyridine (DMAP) in dichloromethane at room temperature to give intermediate IV.

Scheme 2

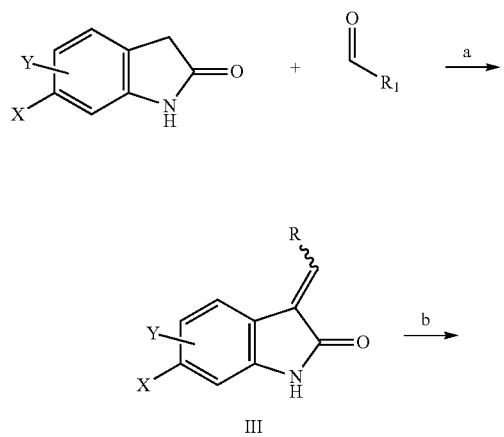

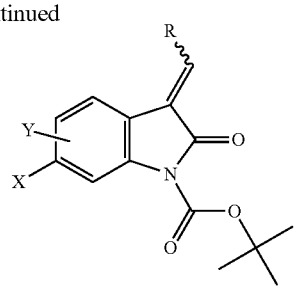

Reagents and conditions:
a) pyrrolidine or piperidine, MeOH, 50° C., 3 h;
b) Boc₂O, DAMP (cat.), CH₂Cl₂, rt, 2 h As illustrated in Scheme 3, racemic mixture of spiroindolinone intermediates V and V' can be made from of intermediates II and IV by water-induced 1,3-dipolar cylcoaddition reaction of N-(silylmethyl)imine and olefin. Similar cycloaddition reactions have been described by Tsuge, O. et al in *Bull. Chem. Soc. Jpn.*, 59, 2537-2545 (1986). Alternatively, racemic mixture of spiroindolinone intermediates V and V' can be prepared from intermediate III (Scheme 3). A Michael addition reaction between nitromethane and intermediate III in methanol under basic condition can lead to the formation of intermediate VI. The nitro group can be reduced by Zinc and ammonium chloride to give intermediate VII. Finally, a condensation and cyclization reaction of appropriately selected aldehyde and intermediate VII can afford the mixture of spiroindolinone intermediates V and V' together with other racemic diastereomeric pairs in which intermediates V and V' can be separated by flash chromatography.

Scheme 3

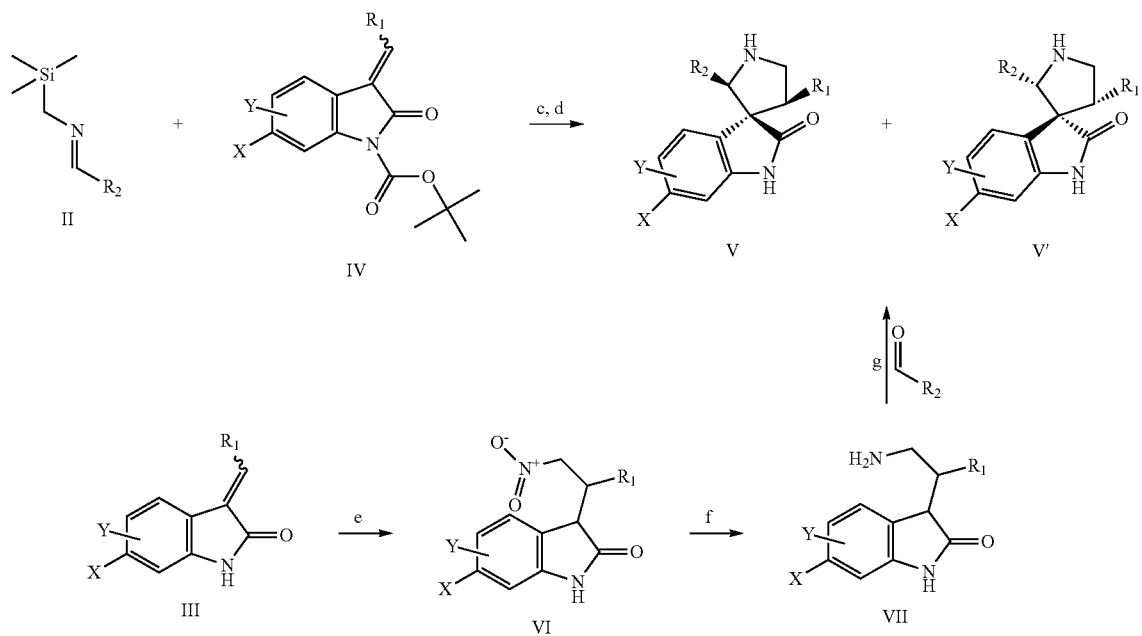

Reagents and conditions: c) HOAc, H2O, HMPA, rt, 18 h; d) TFA, CH2Cl2, rt; e) MeNO₂, NaOMe, MeOH, rt, 2 h; f) Zn, NH₄Cl, MeOH, H₂O, rt, 1 h; g) pyridine, 100° C., 2 h or p-TsOH, toluene, 120° C., 3 h;

Racemic mixtures of intermediates V and V' can be reacted with phosgene to form racemic mixture of intermediates VIII and then subsequently converted to racemic mixtures of analogues IX and IX' in formula I by reaction with selected alkyl and aryl amine or alcohol. Alternatively Racemic mixtures of intermediates V and V' can be directly converted into racemic mixtures of analogues IX and IX' by reaction with appropriately selected alkyl or aryl isocyanate or chloroformate (Scheme 4). Finally, Racemic mixtures of intermediates V and V' can be separated into optically pure or enriched chiral enantiomer IX by chiral Super Fluid Chromatography (SFC) or chiral HPLC or chiral column chromatography. Similarly, other racemic mixture pairs like V and V', VIII and VIII' can also be chirally separated into optically pure or enriched chiral intermediates V or VIII first, then converted into chiral enantiomer IX by procedures outlined in Scheme 4.

Example 1

Preparation of intermediate E/Z-6-chloro-3-(3,3-dimethyl-butylidene)-1,3-dihydro-indol-2-one

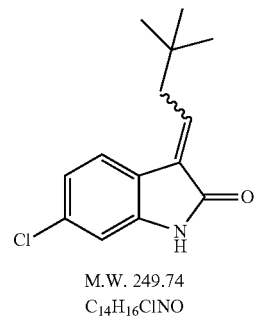

M.W. 249.74
$C_{14}H_{16}ClNO$

Scheme 4

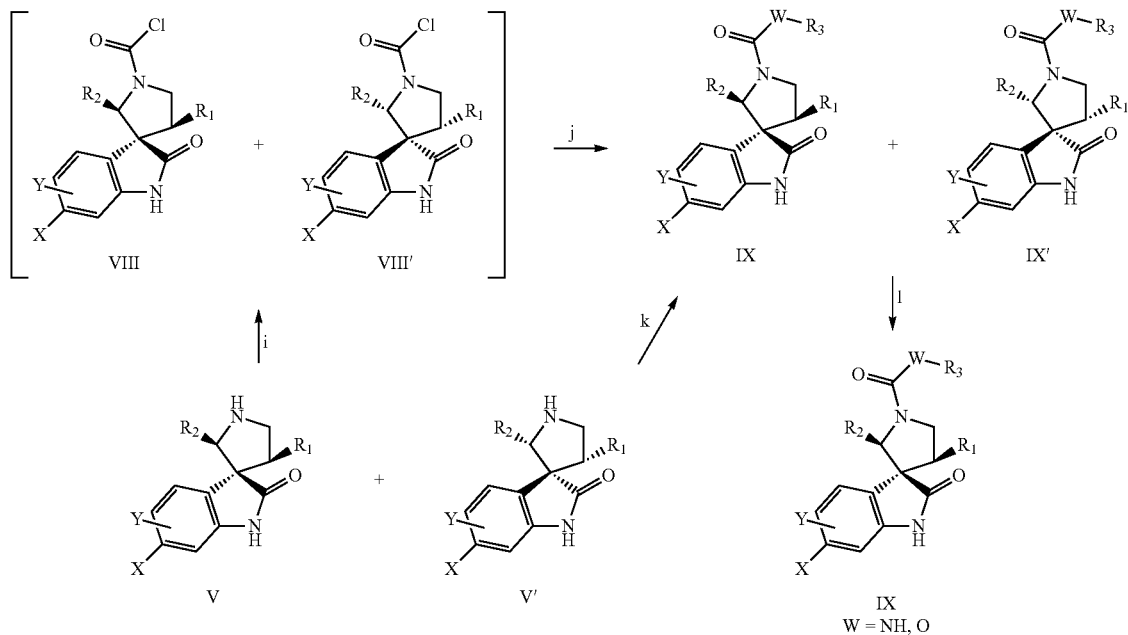

Reagents and conditions: (i) $COCl_2$/aq. $NaHCO_3$/$CH_2Cl_2$, 0° C., 30 min; (j) $H_2NR_3$/TEA/THF or $CH_2Cl_2$, rt, I or $HOR_3$/NaH/DMF, rt, 1 h; (k) $R_3N\!=\!C\!=\!O$/$CH_2Cl_2$, rt, 30 min, or $R_3C(\!=\!O)Cl$/THF, rt, 18 h; (l) SFC chiral separation

EXAMPLES

The compounds of the present invention may be synthesized according to novel techniques. The following examples and references are provided to aid the understanding of the present invention, the true scope of which is set forth in the appended claims.

To the mixture of 6-chlorooxindole (0.26 g, 1.49 mmol) (Crescent) and 3,3-dimethyl-butyraldchyde (0.21 g, 2.09 mmol) (Aldrich) in methanol (20 mL) was added pyrrolidine (0.15 g, 2.09 mmol) (Aldrich) dropwise. The mixture was then heated at 100° C. for 1 h. The mixture was concentrated, and the residue was partitioned between ethyl acetate and water. The organic layer was separated, dried over $Na_2SO_4$, concentrated, and dried in vacuo to give the crude E/Z-6- chloro-3-(3,3-dimethyl-butylidene)-1,3-dihydro-indol-2-one as a white solid (Yield 0.37 g, 100%).

Example 2

Preparation of intermediate racemic 6-chloro-3-(3,3-dimethyl-1-nitromethyl-butyl)-1,3-dihydro-indol-2-one

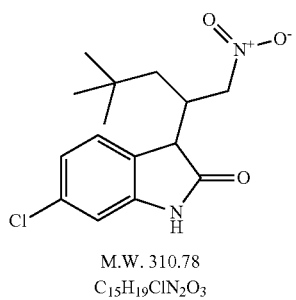

M.W. 310.78
$C_{15}H_{19}ClN_2O_3$

To a solution of nitromethane (Aldrich) (1.7 g, 27 mmol) in methanol (20 mL) was slowly added a methanolic solution (Aldrich, 25 wt. %) of sodium methoxide (5.9 g, 27 mmol). After the mixture was stirred at room temperature for 10 min, a solution of E/Z-6-chloro-3-(3,3-dimethyl-butylidene)-1,3-dihydro-indol-2-one (3.4 g, 14 mmol) in methanol (20 mL) was added. The reaction mixture was stirred at room temperature for 2 h, then acetic acid (2.5 g, 41 mmol) was added. The mixture was concentrated to a small volume, then the residue was partitioned between ethyl acetate and water. The organic layer was separated, the aqueous layer was extracted with ethyl acetate. The organic layers were combined, washed with saturated aqueous $NaHCO_3$, brine, dried over $MgSO_4$, and concentrated. The residue was purified by chromatography (EtOAc:hexanes=1:5, 1:3) to give the racemic 6-chloro-3-(3,3-dimethyl-1-nitromethyl-butyl)-1,3-dihydro-indol-2-one as a white foam (3.8 g, 90%).

Example 3

Preparation of intermediate racemic 3-(1-aminomethyl-3,3-dimethyl-butyl)-6-chloro-1,3-dihydro-indol-2-one

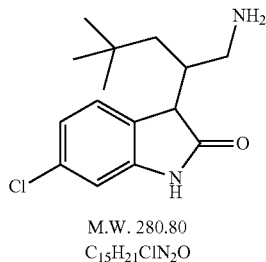

M.W. 280.80
$C_{15}H_{21}ClN_2O$

To a solution of racemic 6-chloro-3-(3,3-dimethyl-1-nitromethyl-butyl)-1,3-dihydro-indol-2-one (3.8 g, 12 mmol) in methanol (80 mL) was added an aqueous solution (20 mL) of ammonium chloride (6.5 g, 122 mmol), followed by the addition of Zinc (Aldrich, activated) (8 g, 122 mmol). The reaction mixture was stirred at room temperature for 0.5 h. The mixture was filtered through a short pad of celite. The filtrate was concentrated to a small volume, then the residue was partitioned between ethyl acetate and water. The organic layer was separated, the aqueous layer was extracted with ethyl acetate. The organic layers were combined, washed with saturated aqueous $NaHCO_3$, brine, dried over $MgSO_4$, and concentrated to give racemic 3-(1-aminomethyl-3,3-dimethyl-butyl)-6-chloro-1,3-dihydro-indol-2-one as a white foam (3.4 g, 99%)

Example 4

Preparation of intermediate E/Z-6-chloro-3-(3,3-dimethyl-butylidene)-2-oxo-2,3-dihydro-indole-1-carboxylic acid tert-butyl ester

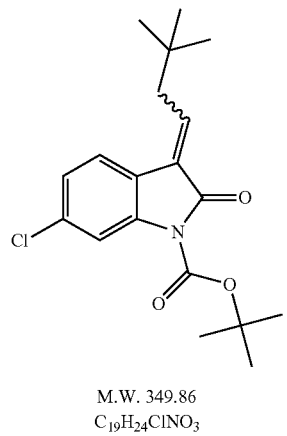

M.W. 349.86
$C_{19}H_{24}ClNO_3$

To a suspension of E/Z-6-chloro-3-(3,3-dimethyl-butylidene)-1,3-dihydro-indol-2-one prepared in Example 1 (5 g, 20 mmol) in dichloromethane (100 mL) was added di-tert-butyl dicarbonate (5 g, 23 mmol) and a catalytic amount of DMAP (30 mg). The reaction mixture was stirred at room temperature for 1 h. Water was added. The organic layer was separated, and aqueous layer was extracted with dichloromethane. The extracts were combined, washed with water, brine, dried over $MgSO_4$, and concentrated to give E/Z-6-chloro-3-(3,3-dimethyl-butylidene)-2-oxo-2,3-dihydro-indole-1-carboxylic acid tert-butyl ester as a white solid (6 g, 85%).

Example 5

Preparation of intermediate [1-(3-chloro-2-fluoro-phenyl)-meth-(E)-ylidene]-trimethylsilanylmethyl-amine

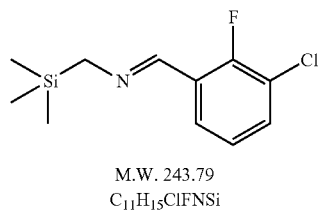

M.W. 243.79
$C_{11}H_{15}ClFNSi$

To a solution of (aminomethyl)trimethylsilane (Fluka) (1.03 g, 10 mmol) in dichloromethane (50 mL) was added 3-chloro-2-fluoro-benzaldehyde (Oakwood) (1.6 g, 10 mmol). The reaction mixture was stirred at room temperature for 3 h. Water was added. The organic layer was separated, washed with brine, dried over MgSO$_4$, and concentrated to give [1-(3-chloro-2-fluoro-phenyl)-meth-(E)-ylidene]-trimethylsilanylmethyl-amine as a colorless oil (2.4 g, 99%).

Example 6

Preparation of intermediate rac-(2'S,3'S,4'S)-6-chloro-2'-(3-chloro-2-fluoro-phenyl)-4'-(2,2-dimethyl-propyl)-1H-spiro[indole-3,3'-pyrrolidin]-2-one

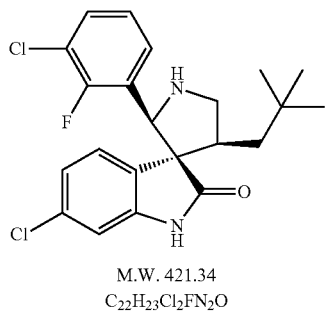

M.W. 421.34
C$_{22}$H$_{23}$Cl$_2$FN$_2$O

Method A.

To a solution of E/Z-6-chloro-3-(3,3-dimethyl-butylidene)-2-oxo-2,3-dihydro-indole-1-carboxylic acid tert-butyl ester prepared in Example 4 (2.5 g, 7.1 mmol) in hexamethylphosphoramide (30 mL) was added [1-(3-chloro-2-fluoro-phenyl)-meth-(E)-ylidene]-trimethylsilanylmethyl-amine prepared in Example 5 (2.4 g, 9.9 mmol), acetic acid (0.6 g, 10 mmol) and H$_2$O (0.2 g, 11 mmol) sequentially. The reaction mixture was stirred at room temperature for 24 h. Water was added. The mixture was extracted with ethyl acetate. The organic layer was separated, and aqueous layer was extracted with ethyl acetate. The organic layers were combined, washed with water twice, dried over MgSO$_4$, then concentrated. The residue was dissolved into dichloromethane (20 mL), and trifluoroacetic acid (10 mL) was added. The reaction mixture was stirred at room temperature for 1 h. The mixture was concentrated, and the residue was partitioned between ethyl acetate and aqueous saturated NaHCO$_3$ solution. The organic layer was separated, dried over MgSO$_4$, then concentrated. The residue was purified by chromatography (50-100% EtOAc in hexanes) to give rac-(2'S,3'S,4'S)-6-chloro-2'-(3-chloro-2-fluoro-phenyl)-4'-(2,2-dimethyl-propyl)-1H-spiro[indole-3,3'-pyrrolidin]-2-one as a white solid (Yield, 0.6 g, 20%).

Method B.

To a solution of racemic 3-(1-aminomethyl-3,3-dimethyl-butyl)-6-chloro-1,3-dihydro-indol-2-one prepared in Example 3 (1.2 g, 4.3 mmol) in pyridine (50 mL) was added 3-chloro-2-fluoro-benzaldehyde (Oakwood) (0.68 g, 4.3 mmol). The reaction mixture was heated at 100° C. for 2 h. The mixture was cooled to room temperature and concentrated. The residue was dissolved into ethyl acetate, washed with aqueous saturated CuSO$_4$ solution, and brine. The organic layer was separated, dried over MgSO$_4$, and concentrated. The residue was purified by chromatography (50-100% EtOAc in hexanes) to give rac-(2'S,3'S,4'S)-6-chloro-2'-(3-chloro-2-fluoro-phenyl)-4'-(2,2-dimethyl-propyl)-1H-spiro[indole-3,3'-pyrrolidin]-2-one as a white solid (Yield, 0.29 g, 16%).

Example 7

Preparation of intermediate 2-((S)-2,2-dimethyl-[1,3]-dioxolan-4-yl)-ethylamine

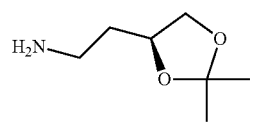

M.W. 145.20 C$_7$H$_{15}$NO$_2$

Step A.

To a solution of (4S)-(+)-4-(2-hydroxyethyl)-2,2-dimethyl-1,3-dioxolane (Aldrich) (21.1 g, 0.14 mol) and triethylamine (40 mL, 0.28 mol) in dichloromethane (250 mL) at 0° C. was added methanesulfonyl chloride (13.4 mL, 0.17 mol) dropwise. The reaction mixture was stirred at 0° C. for 1.5 h, then water was added. The organic layer was separated, washed with water, brine, dried over MgSO$_4$, concentrated to give methanesulfonic acid 2-((S)-2,2-dimethyl-[1,3]dioxolan-4-yl)-ethyl ester as a yellow oil (31.7 g, 98%).

Step B.

To a solution of methanesulfonic acid 2-((S)-2,2-dimethyl-[1,3]dioxolan-4-yl)-ethyl ester (31.7 g, 0.14 mol) in N,N-dimethylformamide (200 mL) was added NaN$_3$ (46 g, 0.71 mol). The reaction mixture was stirred at room temperature for 70 h. Then the mixture was partitioned between ethyl acetate and water. The organic layer was separated, washed with water, brine several times, dried over MgSO$_4$, concentrated to give (S)-4-(2-azido-ethyl)-2,2-dimethyl-[1,3]dioxolane as a yellow oil (21.3 g, 88%).

Step C.

A suspension of (S)-4-(2-azido-ethyl)-2,2-dimethyl-[1,3]dioxolane as a yellow oil (18.7 g, 0.11 mol) and PtO$_2$ (2.5 g) in ethyl acetate (100 mL) was vigorously shaken in a Parr under atmosphere of H$_2$ (50 psi) for 18 h. The mixture was filtered through a short pad of celite. The filtrate was concentrated to give 2-((S)-2,2-dimethyl-[1,3]dioxolan-4-yl)-ethylamine as a colorless oil (14 g, 88%).

Example 8

Preparation of intermediate rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride

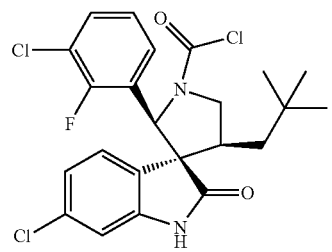

M.W. 483.80 C$_{23}$H$_{22}$Cl$_3$FN$_2$O$_2$

To a solution of rac-(2'S,3'S,4'S)-6-chloro-2'-(3-chloro-2-fluoro-phenyl)-4'-(2,2-dimethyl-propyl)-1H-spiro[indole-3, 3'-pyrrolidin]-2-one prepared in Example 6 (0.12 g, 0.28 mmol) in dichloromethane (3 mL) was added saturated aqueous NaHCO$_3$ solution (3 mL). The temperature of the mixture was lowered to 0° C., and a toluene solution (Aldrich, 20%) of phosgene (0.27 mL, 0.51 mmol) was added dropwise via a syringe. The reaction mixture was stirred at room temperature for 30 min, then diluted dichloromethane. The organic layer was separated, the aqueous layer was extracted with dichloromethane twice. The combined organic layers were washed with water, brine, dried over MgSO$_4$, and concentrated to give crude rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride as a light yellow oil, which was used in the next step without further purification (0.14 g, 100%).

Example 9

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide

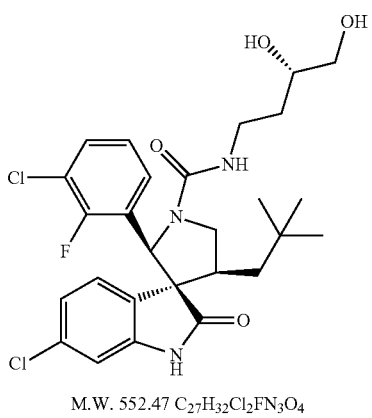

M.W. 552.47 C$_{27}$H$_{32}$Cl$_2$FN$_3$O$_4$

To a solution of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride (0.14 g, 0.28 mmol) in tetrahydrofuran (5 mL) was added 2-((S)-2,2-dimethyl-[1,3]dioxolan-4-yl)-ethylamine prepared in Example 7 (49 mg, 0.34 mmol) and triethylamine (0.078 mL, 0.56 mmol). The reaction mixture was stirred at room temperature for 1 h. An aqueous HCl solution (1 N, 2 mL) was added. The reaction mixture was stirred at room temperature for 0.5 h. The solvents were removed and the residue was partitioned between ethyl acetate and saturated aqueous NaHCO$_3$ solution. The organic layer was separated, and the aqueous layer was extracted with ethyl acetate. The organic layers were combined, washed with water, brine, dried over MgSO$_4$, and concentrated. The residue was triturated with dichlormethane and hexanes to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide as a white solid (Yield 75 mg, 50%).

HRMS(ES) m/z Calcd for C$_{27}$H$_{32}$Cl$_2$FN$_3$O$_4$+H [(M+H): 554.1784; Found: 554.1785.

Example 10

Preparation of chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide

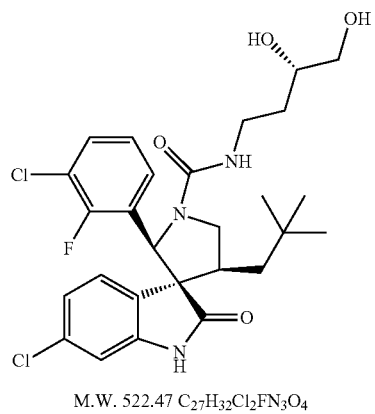

M.W. 522.47 C$_{27}$H$_{32}$Cl$_2$FN$_3$O$_4$

Rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide (70 mg) was separated by chiral SFC chromatography to provide chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide as a white solid (25 mg, 36%) and chiral (2'R,3'R,4'R)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide as a white solid (29 mg, 41%).

Example 11

Preparation of rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid ethyl ester

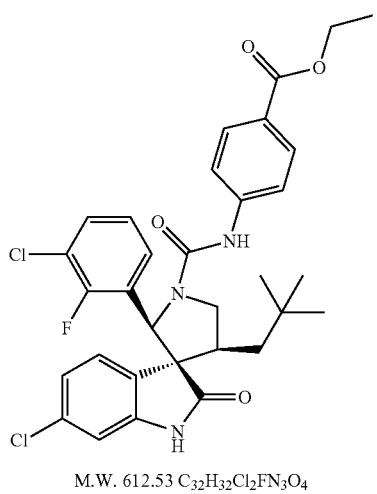

M.W. 612.53 C$_{32}$H$_{32}$Cl$_2$FN$_3$O$_4$

To a solution of rac-(2'S,3'S,4'S)-6-chloro-2'-(3-chloro-2-fluoro-phenyl)-4'-(2,2-dimethyl-propyl)-1H-spiro[indole-3,3'-pyrrolidin]-2-one prepared in Example 6 (0.14 g, 0.33 mmol) in dichloromethane (5 mL) was added 4-isocyanato-benzoic acid ethyl ester (Aldrich) (64 mg, 0.33 mmol) and triethylamine (0.092 mL, 0.66 mmol). The reaction mixture was stirred at room temperature for 30 min. Water was added. The mixture was partitioned between dichlormethane and water. The organic layer was separated, and aqueous layer was extracted with dichlormethane. The organic layers were combined, washed with water, brine, dried over $MgSO_4$, and concentrated. The residue was purified by chromatography (15% EtOAc in hexanes) to give rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid ethyl ester as a white solid (0.1 g, 50%)

HRMS(ES$^+$) m/z Calcd for $C_{32}H_{32}Cl_2FN_3O_4$+H [(M+H): 614.1784; Found: 614.1782.

Example 12

Preparation of rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid methyl ester

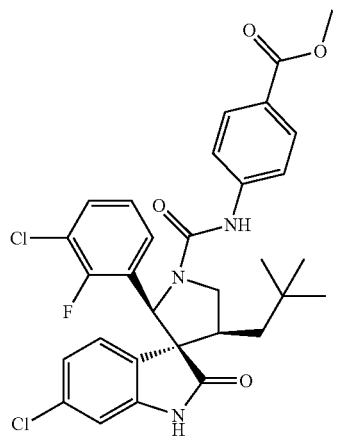

M.W. 598.50 $C_{31}H_{30}Cl_2FN_3O_4$

A mixture of rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid ethyl ester (80 mg, 0.13 mmol) in methanol (3 mL) was added an aqueous solution (1 N) of NaOH (3 mL, 3 mmol). The reaction mixture was stirred at room temperature for 20 h. The mixture was concentrated. The residue was partitioned between ethyl acetate and water. The organic layer was separated, and the aqueous layer was extracted with ethyl acetate. The organic layers were combined, washed with water, brine, dried over $MgSO_4$, and concentrated to give rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid methyl ester as a white solid (Yield 60 mg, 77%).

HRMS(ES) m/z Calcd for $C_{31}H_{30}Cl_2FN_3O_4$+H [(M+H): 586.1471; Found: 586.1473.

Example 13

Preparation of rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid

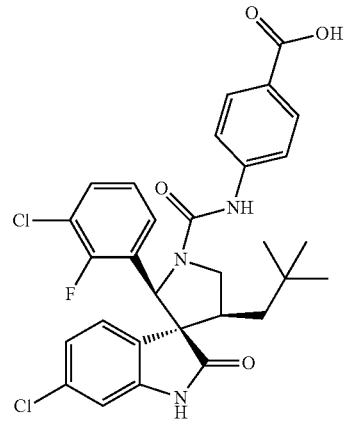

M.W. 584.47 $C_{30}H_{28}Cl_2FN_3O_4$

A mixture of rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid methyl ester (40 mg, 0.07 mmol) in tetrahydrofuran (5 mL) and water (5 mL) was added an aqueous solution (1 N) of LiOH (0.7 mL, 0.7 mmol). The reaction mixture was heated at 70° C. for 2 h. The mixture was concentrated. The residue was dissolved into water. The "pH" of the mixture was adjusted to 5-6 by addition of aqueous HCl solution. The mixture was extracted with ethyl acetate. The organic layer was separated, and the aqueous layer was extracted with ethyl acetate again. The organic layers were combined, washed with water, brine, dried over $MgSO_4$, and concentrated. The residue was triturated with dichlormethane and hexanes to give rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid as a white solid (Yield 25 mg, 65%).

HRMS(ES$^+$) m/z Calcd for $C_{30}H_{28}Cl_2FN_3O_4$+H [(M+H): 586.1471; Found: 586.1473.

Example 14

Preparation of chiral 4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid

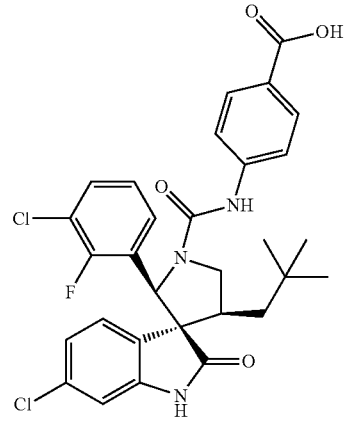

M.W. 584.47 $C_{30}H_{28}Cl_2FN_3O_4$

Rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid (50 mg) was separated by chiral SFC chromatography to provide chiral 4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]amino}-benzoic acid as a white solid (18 mg, 36%) and chiral 4-{[(2'R,3'R,4'R)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid as a white solid (21 mg, 41%).

Example 15

Preparation of intermediate [1-(3-chloro-phenyl)-meth-(E)-ylidene]-trimethylsilanylmethyl-amine

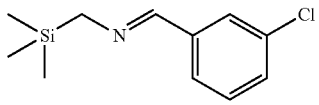

M.W. 225.80 C$_{11}$H$_{16}$ClNSi

To a solution of (aminomethyl)trimethylsilane (Fluka) (1.6 g, 16 mmol) in dichloromethane (100 mL) was added 3-chloro-benzaldehyde (Aldrich) (1.9 g, 14 mmol). The reaction mixture was stirred at room temperature for 3 h. Water was added. The organic layer was separated, washed with brine, dried over MgSO$_4$, and concentrated to give [1-(3-chloro-phenyl)-meth-(E)-ylidene]-trimethylsilanylmethyl-amine as a colorless oil (3 g, 95%).

Example 16

Preparation of intermediate rac-(2'R,3'S,4'S)-6-chloro-2'-(3-chloro-phenyl)-4'-(2,2-dimethyl-propyl)-1H-spiro[indole-3,3'-pyrrolidin]-2-one

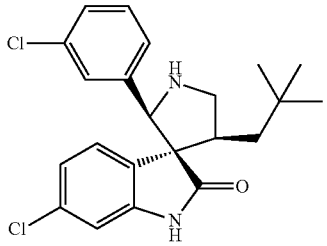

M.W. 403.35 C$_{22}$H$_{23}$Cl$_2$N$_2$O

To a solution of E/Z-6-chloro-3-(3,3-dimethyl-butylidene)-2-oxo-2,3-dihydro-indole-1-carboxylic acid tert-butyl ester prepared in Example 4 (2.4 g, 6.9 mmol) in hexamethylphosphoramide (30 mL) was added [1-(3-chloro-phenyl)-meth-(E)-ylidene]-trimethylsilanylmethyl-amine prepared in Example 14 (3 g, 13 mmol), acetic acid (0.6 g, 10 mmol) and H$_2$O (0.2 g, 11 mmol) sequentially. The reaction mixture was stirred at room temperature for 24 h. Water was added. The mixture was extracted with ethyl acetate. The organic layer was separated, and aqueous layer was extracted with ethyl acetate. The organic layers were combined, washed with water twice, dried over MgSO$_4$, then concentrated. The residue was dissolved into dichloromethane (10 mL), and trifluoroacetic acid (5 mL) was added. The reaction mixture was stirred at room temperature for 1 h. The mixture was concentrated, and the residue was partitioned between ethyl acetate and aqueous saturated NaHCO$_3$ solution. The organic layer was separated, dried over MgSO$_4$, then concentrated. The residue was purified by chromatography (50-75% EtOAc in hexanes) to give rac-(2'R,3'S,4'S)-6-chloro-2'-(3-chloro-phenyl)-4'-(2,2-dimethyl-propyl)-1H-spiro[indole-3,3'-pyrrolidin]-2-one as a white solid (Yield, 0.8 g, 29%).

Example 17

Preparation of intermediate rac-(2'R,3'S,4'S)-6-chloro-2'-(3-chloro-phenyl)-4'-(2,2-dimethyl-propyl)-2-oxo-1,2-dihydro-spiro[indole-3,3'-pyrrolidine]-1'-carbonyl chloride

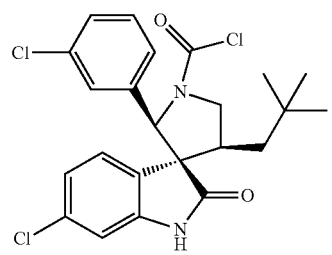

M.W. 465.81 C$_{23}$H$_{23}$Cl$_3$N$_2$O$_2$

In a manner similar to the method described in Example 8, rac-(2'R,3'S,4'S)-6-chloro-2'-(3-chloro-phenyl)-4'-(2,2-dimethyl-propyl)-1H-spiro[indole-3,3'-pyrrolidin]-2-one prepared in Example 16 (0.3 g, 0.74 mmol) was reacted with a toluene solution (Aldrich, 20%) of phosgene (0.7 mL, 1.3 mmol) and saturated aqueous NaHCO$_3$ solution (5 mL) in dichloromethane (5 mL) to give rac-(2'R,3'S,4'S)-6-chloro-2'-(3-chloro-phenyl)-4'-(2,2-dimethyl-propyl)-2-oxo-1,2-dihydro-spiro[indole-3,3'-pyrrolidine]-1'-carbonyl chloride as a yellow oil (Yield, 0.34 g, 100%), which was used in the next step without further purification.

Example 18

Preparation of rac-(2'R,3'S,4'S)-6-chloro-2'-(3-chloro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide

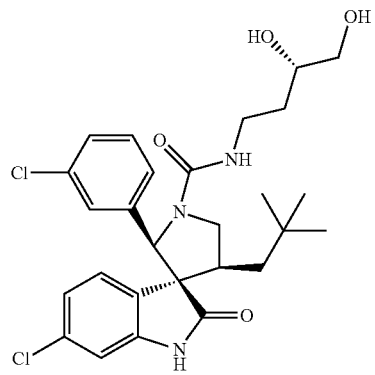

M.W. 534.48 C$_{27}$H$_{33}$Cl$_2$N$_3$O$_4$

In a manner similar to the method described in Example 9, rac-(2'R,3'S,4'S)-6-chloro-2'-(3-chloro-phenyl)-4'-(2,2-dimethyl-propyl)-2-oxo-1,2-dihydro-spiro[indole-3,3'-pyrrolidine]-1'-carbonyl chloride (0.34 g, 0.74 mmol) was reacted with 2-((S)-2,2-dimethyl-[1,3]dioxolan-4-yl)-ethylamine prepared in Example 7 (0.13 g, 0.89 mmol) and triethylamine in tetrahydrofuran, then reacted with aqueous HCl solution in tetrahydrofuran to give rac-(2'R,3'S,4'S)-6-chloro-2'-(3-chloro-phenyl)-4'-(2,2-dimethyl-propyl)-2-oxo-1,2-dihydro-spiro[indole-3,3'-pyrrolidine]-l'-carboxylic acid ((S)-3,4-dihydroxy-butyl)-amide as a white solid (Yield, 75 mg, 19%).

HRMS(ES+) m/z Calcd for $C_{27}H_{33}Cl_2N_3O_4$+H [(M+H)]: 554.1784; Found: 554.1785.

Example 19

Preparation of rac-4-{[(2'R,3'S,4'S)-6-chloro-2'-(3-chloro-phenyl)-4'-(2,2-dimethyl-propyl)-2-oxo-1,2-dihydro-spiro[indole-3,3'-pyrrolidin]e-1'-carbonyl)-amino}-benzoic acid methyl ester

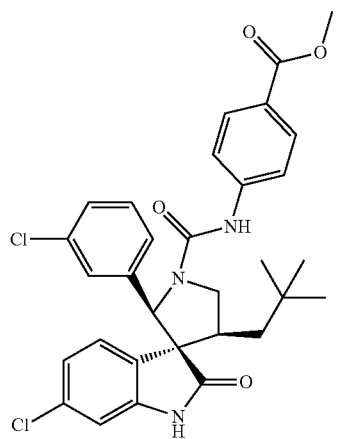

M.W. 580.51 $C_{31}H_{31}Cl_2N_3O_4$

In a manner similar to the method described in Example 11, rac-(2'R,3'S,4'S)-6-chloro-2'-(3-chloro-phenyl)-4'-(2,2-dimethyl-propyl)-1H-spiro[indole-3,3'-pyrrolidin]-2-one prepared in Example 16 (0.3 g, 0.74 mmol) was reacted with 4-isocyanato-benzoic acid methyl ester (0.14 g, 0.82 mmol) and triethylamine in dichlormethane to give rac-4-{[(2'R,3'S, 4'S)-6-chloro-2'-(3-chloro-phenyl)-4'-(2,2-dimethyl-propyl)-2-oxo-1,2-dihydro-spiro[indole-3,3'-pyrrolidin]e-1'-carbonyl]-amino}-benzoic acid methyl ester as a white solid (Yield, 30 mg, 7%).

HRMS(ES+) m/z Calcd for $C_{31}H_{31}Cl_2N_3O_4$+H [(M+H)]: 554.1784; Found: 554.1785.

Example 20

Preparation of rac-4-{[(2'R,3'S,4'S)-6-chloro-2'-(3-chloro-phenyl)-4'-(2,2-dimethyl-propyl)-2-oxo-1,2-dihydro-spiro[indole-3,3'-pyrrolidin]e-1'-carbonyl]-amino}-benzoic acid

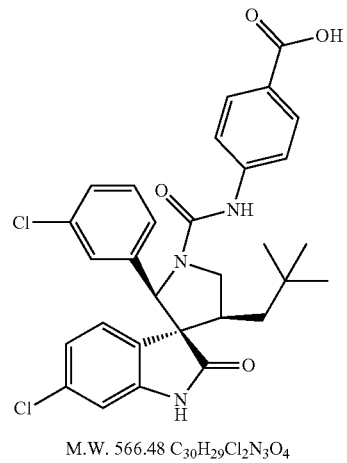

M.W. 566.48 $C_{30}H_{29}Cl_2N_3O_4$

In a manner similar to the method described in Example 13, rac-4-{[(2'R,3'S,4'S)-6-chloro-2'-(3-chloro-phenyl)-4'-(2,2-dimethyl-propyl)-2-oxo-1,2-dihydro-spiro[indole-3,3'-pyrrolidin]e-1'-carbonyl]-amino}-benzoic acid methyl ester (50 mg, 0.086 mmol) was heated with aqueous LiOH (1 N, 0.9 mL, 0.9 mmol) in tetrahydrofuran (3 mL), water (3 mL), and methanol (1 mL) at 90° C. for 3 h to give rac-4-{[(2'S,3'S, 4'S)-6-chloro-2'-(3-chloro-phenyl)-4'-(2,2-dimethyl-propyl)-2-oxo-1,2-dihydro-spiro[indole-3,3'-pyrrolidin]e-1'-carbonyl]-amino}-benzoic acid as a white solid (Yield, 30 mg, 60%).

HRMS(ES+) m/z Calcd for $C_{30}H_{29}Cl_2N_3O_4$+H [(M+H): 586.1471; Found: 586.1473.

Example 21

Preparation of rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid methyl ester

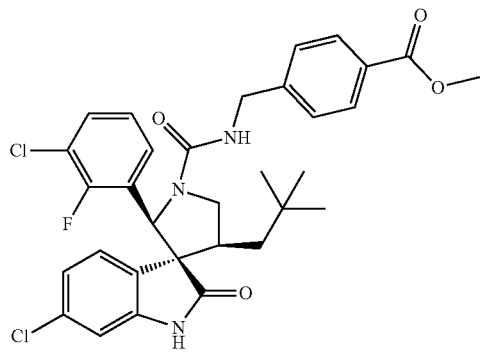

M.W. 612.53 $C_{32}H_{32}Cl_2FN_3O_4$

In a manner similar to the method described in Example 9, rac-(2'5,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride prepared in Example 8 (0.23 g, 0.47 mmol) was reacted with methyl 4-(aminomethyl)benzoate hydrochloride (Aldrich) (0.19 g, 0.94 mmol) and triethylamine to give rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid methyl ester as a white solid (Yield, 80 mg, 28%).

HRMS(ES$^+$) m/z Calcd for $C_{32}H_{32}Cl_2FN_3O_4$+H [(M+H)]: 554.1784; Found: 554.1785.

Example 22

Preparation of rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid

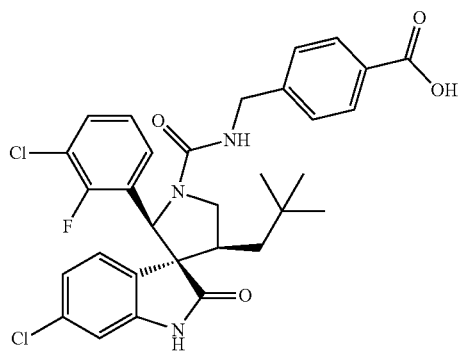

M.W. 598.50 $C_{31}H_{30}Cl_2FN_3O_4$

In a manner similar to the method described in Example 13, rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid methyl ester (60 mg, 0.09 mmol) was heated with aqueous LiOH (1 N, 0.9 mL, 0.9 mmol) in tetrahydrofuran (3 mL), water (3 mL and methanol (1 mL) at 70° C. for 1 h to give rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid as a white solid (Yield, 50 mg, 93%).

HRMS(ES$^+$) m/z Calcd for $C_{31}H_{30}Cl_7FN_3O_4$+H [(M+H)]: 586.1471; Found: 586.1473.

Example 23

Preparation of chiral 4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid

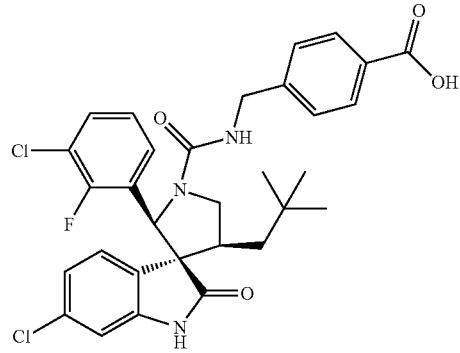

M.W. 598.20 $C_{31}H_{30}Cl_2FN_3O_4$

Rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid (230 mg) was separated by chiral SFC chromatography to provide chiral 4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid as a white solid (92 mg, 40%) and chiral 4-({[(2'R,3'R,4'R)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid as a while solid (93 mg, 40%).

Example 24

Preparation of rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-piperidine-1-carboxylic acid tert-butyl ester

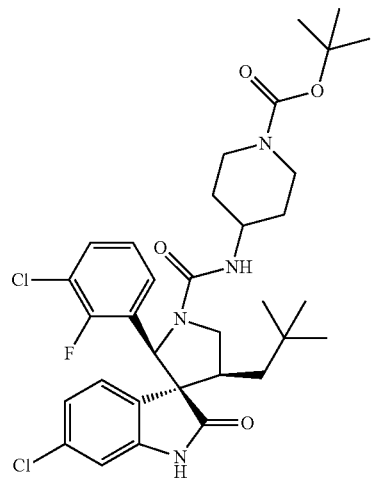

M.W. 647.62 $C_{33}H_{41}Cl_2FN_4O_4$

In a manner similar to the method described in Example 9, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride prepared in Example 8 (0.97 g, 2 mmol) was reacted with 4-amino-piperidine-1-carboxylic acid tert-butyl ester (Aldrich) (0.45 g, 2.3 mmol) and triethylamine to give rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-piperidine-1-carboxylic acid tert-butyl ester as a white solid (Yield, 0.4 g, 31%).

HRMS(ES$^+$) m/z Calcd for $C_{33}H_{41}Cl_2FN_4O_4$+H [(M+H)]: 554.1784; Found: 554.1785.

Example 25

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid piperidin-4-ylamide trifluoroacetic acid

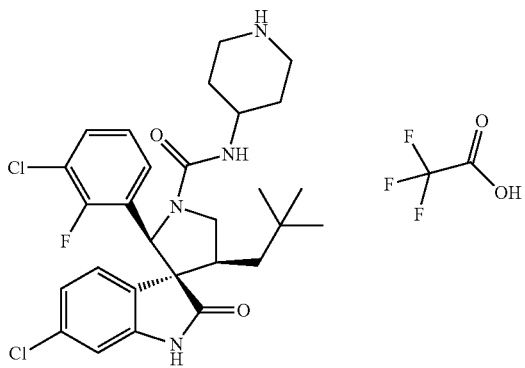

M.W. 547.50 $C_{28}H_{33}Cl_2FN_4O_2 \cdot C_2HF_3O_2$

A solution of rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-piperidine-1-carboxylic acid tert-butyl ester (0.17 g, 0.25 mmol) in dichloromethane (1 mL) was added trifluoroacetic acid (1 mL). The reaction mixture was stirred at room temperature for 0.5 h, then concentrated. The residue was then triturated with ethyl ether hexanes, concentrated, dried in vacuo to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid piperidin-4-ylamide trifluoroacetic acid as a white solid (0.17 g, 100%).

HRMS(ES$^+$) m/z Calcd for $C_{28}H_{33}Cl_2FN_4O_2$+H [(M+H)]: 554.1784; Found: 554.1785.

Example 26

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-yl)-amide

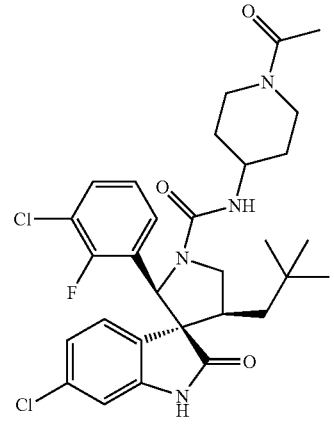

M.W. 589.54 $C_{30}H_{35}Cl_2FN_4O_3$

To a solution of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid piperidin-4-ylamide trifluoroacetic acid (80 mg, 0.12 mmol) in tetrahydrofuran (2 mL) at 0° C. was added triethylamine (0.042 mL, 0.3 mmol) and acetyl chloride (10.4 mg, 0.13 mmol). The mixture was stirred at room temperature for 0.5 h. The mixture was concentrated, and the residue was partitioned between ethyl acetate and water. The organic layer was separated, washed with water, brine, dried over MgSO$_4$, and concentrated. The residue was recrystallized in dichloromethane and hexanes to give as rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-yl)-amide as a white solid (65 mg, 92%)

HRMS(ES$^+$) m/z Calcd for $C_{30}H_{35}Cl_2FN_4O_3$+H [(M+H)]: 554.1784; Found: 554.1785.

Example 27

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide

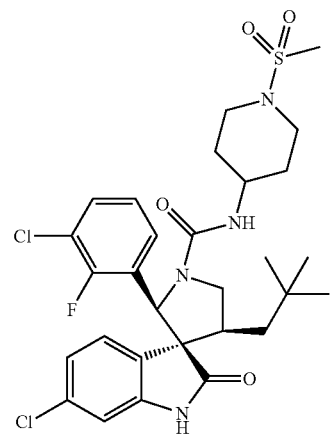

M.W. 625.59 $C_{29}H_{35}Cl_2FN_4O_4S$

To a solution of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid piperidin-4-ylamide trifluoroacetic acid prepared in Example 24 (50 mg, 0.08 mmol) in dichlormethane (10 mL) at 0° C. was added triethylamine (0.026 mL, 0.19 mmol) and methanesulfonyl chloride (10 mg, 0.08 mmol). The mixture was stirred at room temperature for 0.5 h. The mixture was concentrated, and the residue was partitioned between ethyl acetate and water. The organic layer was separated, washed with water, brine, dried over MgSO$_4$, and concentrated. The residue was purified by chromatography (70% EtOAc in hexanes) to give as rac-(2'S, 3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide as a white solid (30 mg, 63%)

HRMS(ES$^+$) m/z Calcd for C$_{29}$H$_{35}$Cl$_2$FN$_4$O$_4$S+H [(M+H)]: 554.1784; Found: 554.1785.

Example 28

Preparation of chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide

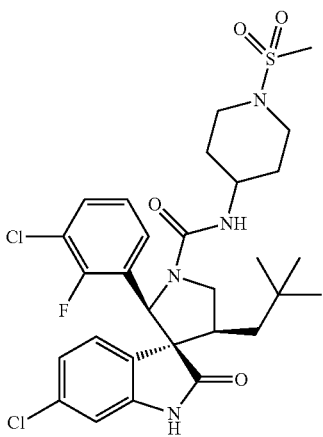

M.W. 625.59 C$_{29}$H$_{35}$Cl$_2$FN$_4$O$_4$S

Rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide (150 mg) was separated by chiral SFC chromatography to provide chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide as a white solid (66 mg, 44%) and chiral (2'R,3'R,4'R)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide as a white solid (58 mg, 39%).

Example 29

Preparation of intermediate 4-(tert-butyl-dimethyl-silanyloxy)-3,3-dimethyl-butyraldehyde

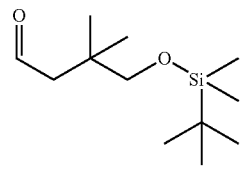

M.W. 343.59 C$_{18}$H$_{37}$NO$_3$Si

Step A

A mixture of 2,2-dimethyl-propane-1,3-diol (Aldrich) (10 g, 96 mmol) and imidazole (9.8 g, 140 mmol) in dichloromethane (200 mL) was added tert-butyldimethylchlorosilane (15.9 g, 10.6 mmol). The reaction mixture was stirred at room temperature for 0.5 h. Water was added. The organic layer was separated, the aqueous layer was then extracted with dichloromethane. The combined organic layers were washed with brine, dried over MgSO$_4$, concentrated to give 3-(tert-butyl-dimethyl-silanyloxy)-2,2-dimethyl-propan-1-ol as a colorless oil (20.4 g, 97%).

Step B

To the solution of 3-(tert-butyl-dimethyl-silanyloxy)-2,2-dimethyl-propan-1-ol (20.4 g, 93 mmol) and triethylamine (26 g, 186 mmol) in dichloromethane (200 mL) at 0° C. was added a dichlormethane solution (20 mL) of methanesulfonyl chloride (Aldrich) (8.69 mL, 112 mmol). The reaction mixture was stirred at 0° C. for 2 h. Water was added. Organic layer was separated, the aqueous layer was extracted with dichlormethane. The combined organic layers were washed with diluted aqueous HCl solution, saturated aqueous NaHCO$_3$ solution, brine, dried over MgSO$_4$, and concentrated to give methanesulfonic acid 3-(tert-butyl-dimethyl-silanyloxy)-2,2-dimethyl-propyl ester as a yellow oil (24 g, 87%).

Step C

To the solution of methanesulfonic acid 3-(tert-butyl-dimethyl-silanyloxy)-2,2-dimethyl-propyl ester (5 g, 16.8 mmol) in anhydrous dimethyl sulfoxide (50 mL) was added KCN (2.85 g, 44 mmol). The reaction mixture was heated at 120° C. for 16 h. The mixture was cooled, and water was added. The mixture was extracted with ethyl acetate twice. The combined organic layers were washed with saturated aqueous NaHCO$_3$ solution, brine, dried over MgSO$_4$, and concentrated. The residue was purified by chromatography (EtOAc:hexanes=1:4) to give 4-(tert-butyl-dimethyl-silanyloxy)-3,3-dimethyl-butyronitrile as a yellow oil (2.2 g, 57%).

Step D

To a solution of 4-(tert-butyl-dimethyl-silanyloxy)-3,3-dimethyl-butyronitrile (2.2 g, 9.67 mmol) (Aldrich) in dichloromethane (20 mL) at −78° C. was added a toluene solution (1 M) of DIBAL (10.6 mL, 10.6 mmol) dropwise. The reaction mixture was stirred at 0° C. for 3 h. The mixture was poured into aqueous saturated NH$_4$Cl solution. The organic layer was separated, and the aqueous layer was extracted with ethyl acetate. The organic layers were combined, washed with brine, dried over MgSO$_4$, and concentrated. The residue was purified by chromatography (EtOAc:hexanes=1:4) to give 4-(tert-butyl-dimethyl-silanyloxy)-3,3-dimethyl-butyraldehyde as a colorless oil (Yield: 0.84 g, 38%).

Example 30

Preparation of intermediate E/Z-3-[4-(tert-butyl-dimethyl-silanyloxy)-3,3-dimethyl-butylidene]-6-chloro-1,3-dihydro-indol-2-one

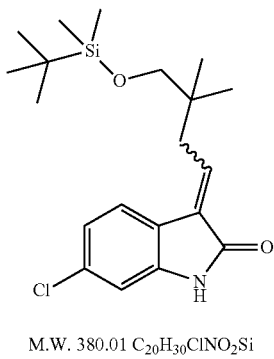

M.W. 380.01 $C_{20}H_{30}ClNO_2Si$

To the mixture of 6-chlorooxindole (2.1 g, 12.6 mmol) (Crescent) and 4-(tert-butyl-dimethyl-silanyloxy)-3,3-dimethyl-butyraldehyde (2.9 g, 12.6 mmol) in methanol (80 mL) was added a methanolic solution (25%, Aldrich) of sodium methoxide (4.08 g, 18.9 mmol) dropwise. The reaction mixture was stirred at room temperature for 10 min. The solvent was removed, and the residue was partitioned between ethyl acetate and water. The organic layer was separated, dried over $Na_2SO_4$, and concentrated. The residue was purified by chromatography (20% EtOAc in hexanes) to give E/Z-3-[4-(tert-butyl-dimethyl-silanyloxy)-3,3-dimethyl-butylidene]-6-chloro-1,3-dihydro-indol-2-one as a yellow oil (Yield 4.1 g, 84%).

Example 31

Preparation of intermediate E/Z-3-[4-(tert-butyl-dimethyl-silanyloxy)-3,3-dimethyl-butylidene]-6-chloro-2-oxo-2,3-dihydro-indole-1-carboxylic acid tert-butyl ester

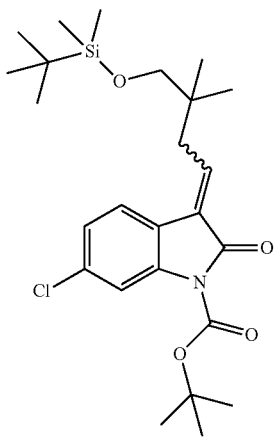

M.W. 480.12 $C_{25}H_{38}ClNO_4Si$

To a suspension of E/Z-3-[4-(tert-butyl-dimethyl-silanyloxy)-3,3-dimethyl-butylidene]-6-chloro-1,3-dihydro-indol-2-one (4.0 g, 10.6 mmol) in dichloromethane (200 mL) was added di-tert-butyl dicarbonate (2.53 g, 11.6 mmol) and a catalytic amount of DMAP (30 mg). The reaction mixture was stirred at room temperature for 1 h. Water was added. The organic layer was separated, and aqueous layer was extracted with dichloromethane. The extracts were combined, washed with water, brine, dried over $MgSO_4$, and concentrated. The residue was purified by chromatography (20% EtOAc in hexanes) to give E/Z-3-[4-(tert-butyl-dimethyl-silanyloxy)-3,3-dimethyl-butylidene]-6-chloro-2-oxo-2,3-dihydro-indole-1-carboxylic acid tert-butyl ester as a yellow oil (5.0 g, 99%).

Example 32

Preparation of intermediate rac-(2'S,3'S,4'S)-6-chloro-2'-(3-chloro-2-fluoro-phenyl)-4'-(3-hydroxy-2,2-dimethyl-propyl)-1H-spiro[indole-3,3'-pyrrolidin]-2-one

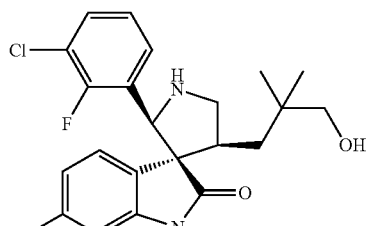

M.W. 437.35 $C_{22}H_{23}Cl_2FN_2O_3$

To a solution of E/Z-3-[4-(tert-butyl-dimethyl-silanyloxy)-3,3-dimethyl-butylidene]-6-chloro-2-oxo-2,3-dihydro-indole-1-carboxylic acid tert-butyl ester prepared in Example 31 (2.5 g, 5.2 mmol) in hexamethylphosphoramide (30 mL) was added [1-(3-chloro-2-fluoro-phenyl)-meth-(E)-ylidene]-trimethylsilanylmethyl-amine prepared in Example 5 (2.9 g, 12 mmol), acetic acid (0.75 g, 12 mmol) and $H_2O$ (0.25 g, 14 mmol) sequentially. The reaction mixture was stirred at room temperature for 24 h. Water was added. The mixture was extracted with ethyl acetate. The organic layer was separated, and aqueous layer was extracted with ethyl acetate. The organic layers were combined, washed with water twice, dried over $MgSO_4$, then concentrated. The residue was dissolved into dichloromethane (10 mL), and trifluoroacetic acid (5 mL) was added. The reaction mixture was stirred at room temperature for 1 h. The mixture was concentrated, and the residue was partitioned between ethyl acetate and aqueous saturated $NaHCO_3$ solution. The organic layer was separated, dried over $MgSO_4$, then concentrated. The residue was dissolved into tetrahydrofuran (5 mL), and saturated aqueous $NaHCO_3$ solution was added (5 mL). The reaction mixture was stirred at room temperature for 1 h. The mixture was concentrated, and the residue was partitioned between ethyl acetate and water. The organic layer was separated, dried over $MgSO_4$, then concentrated. The residue was purified by chromatography (3% MeOH in EtOAc) to give rac-(2'S,3'S,4'S)-6-chloro-2'-(3-chloro-2-fluoro-phenyl)-4'-(3-hydroxy-2,2-dimethyl-propyl)-1H-spiro[indole-3,3'-pyrrolidin]-2-one as a white solid (Yield, 0.25 g, 11%).

Example 33

Preparation of rac-(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidine]-1'-carboxylic acid ((S)-3,4-dihydroxy-butyl)-amide

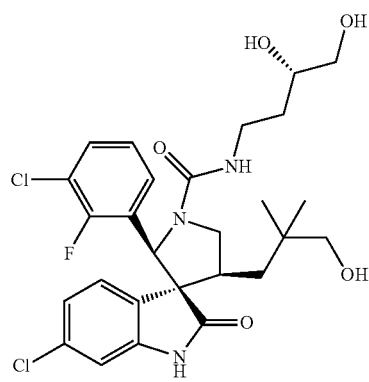

M.W. 568.47 $C_{27}H_{32}Cl_2FN_3O_5$

To a solution of rac-(2'S,3'S,4'S)-6-chloro-2'-(3-chloro-2-fluoro-phenyl)-4'-(3-hydroxy-2,2-dimethyl-propyl)-1H-spiro[indole-3,3'-pyrrolidin]-2-one prepared in Example 32 (60 mg, 0.14 mmol) in dichloromethane (5 mL) was added saturated aqueous $NaHCO_3$ solution (5 mL). The temperature of the mixture was lowered to 0° C., and a toluene solution (Aldrich, 20%) of phosgene (0.13 mL, 0.25 mmol) was added dropwise via a syringe. The reaction mixture was stirred at room temperature for 30 min, then diluted dichloromethane. The organic layer was separated, the aqueous layer was extracted with dichlormethane twice. The combined organic layers were washed with water, brine, dried over $MgSO_4$, and concentrated. The residue was dissolved into tetrahydrofuran (5 mL), and 2-((S)-2,2-dimethyl-[1,3]-dioxolan-4-yl)-ethylamine prepared in Example 7 (24 mg, 0.16 mmol) and triethylamine (0.038 mL, 0.27 mmol) were added sequentially. The reaction mixture was stirred at room temperature for 1 h. An aqueous HCl solution (1 N, 2 mL) was added. The reaction mixture was stirred at room temperature for 1 h. The solvents were removed and the residue was partitioned between ethyl acetate and saturated aqueous $NaHCO_3$ solution. The organic layer was separated, and the aqueous layer was extracted with ethyl acetate. The organic layers were combined, washed with water, brine, dried over $MgSO_4$, and concentrated. The residue was purified by chromatography (15% MeOH in EtOAc) to give rac-(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidine]-1'-carboxylic acid ((S)-3,4-dihydroxy-butyl)-amide as a off white solid (Yield 16 mg, 20%).

HRMS(ES$^+$) m/z Calcd for $C_{27}H_{32}Cl_2FN_3O_5$+H [(M+H)]: 554.1784; Found: 554.1785.

Example 34

Preparation of rac-4-({[(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidin]e-1'-carbonyl]-amino}-methyl)-benzoic acid methyl ester

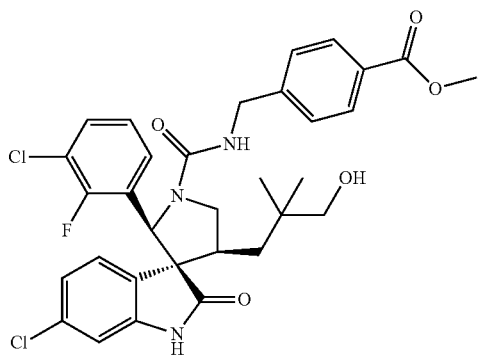

M.W. 628.53 $C_{32}H_{32}Cl_2FN_3O_5$

To a solution of rac-(2'S,3'S,4'S)-6-chloro-2'-(3-chloro-2-fluoro-phenyl)-4'-(3-hydroxy-2,2-dimethyl-propyl)-1H-spiro[indole-3,3'-pyrrolidin]-2-one prepared in Example 32 (0.25 g, 0.57 mmol) in dichloromethane (5 mL) was added saturated aqueous $NaHCO_3$ solution (5 mL). The temperature of the mixture was lowered to 0° C., and a toluene solution (Aldrich, 20%) of phosgene (0.54 mL, 1.0 mmol) was added dropwise via a syringe. The reaction mixture was stirred at room temperature for 30 min, then diluted dichloromethane. The organic layer was separated, the aqueous layer was extracted with dichlormethane twice. The combined organic layers were washed with water, brine, dried over $MgSO_4$, and concentrated. The residue was dissolved into tetrahydrofuran (3 mL) and N,N-dimethylforamide (2 mL), and methyl 4-(aminomethyl)benzoate hydrochloride (Aldrich) (0.23 g, 1.1 mmol) and triethylamine (0.24 mL, 1.7 mmol) were added sequentially. The reaction mixture was stirred at room temperature for 2 h. The solvents were removed, and the residue was partitioned between ethyl acetate and water. The organic layer was separated, and the aqueous layer was extracted with ethyl acetate. The organic layers were combined, washed with water, brine, dried over $MgSO_4$, and concentrated. The residue was purified by chromatography (EtOAc) to give rac-4-({[(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidin]e-1'-carbonyl]-amino}-methyl)-benzoic acid methyl ester as a off white solid (Yield 85 mg, 24%).

HRMS(ES$^+$) m/z Calcd for $C_{32}H_{32}Cl_2FN_3O_5$+H [(M+H)]: 554.1784; Found: 554.1785.

Example 35

Preparation of rac-4-({[(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidin]e-1'-carbonyl]-amino}-methyl)-benzoic acid

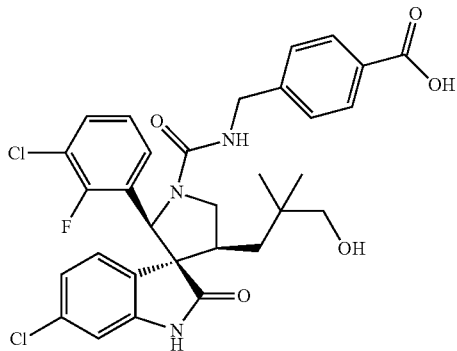

M.W. 614.50 C31H30Cl2FN3O5

In a manner similar to the method described in Example 13, rac-4-({[(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidin]e-1'-carbonyl]-amino}-methyl)-benzoic acid methyl ester (64 mg, 0.1 mmol) was heated with LiOH (24 mg, 1 mmol) in tetrahydrofuran (3 mL), water (3 mL), and methanol (1 mL) at 70° C. for 1 h to give rac-4-({[(2'S,3'S,4'S)-6-chloro-2'43-chloro-2-fluoro-phenyl)-4'-(3-hydroxy-2,2-dimethyl-propyl)-2-oxo-1,2-dihydro-spiro[indole-3,3'-pyrrolidin]e-1'-carbonyl]-amino}-methyl)-benzoic acid as a yellow solid (Yield, 61 mg, 97%).

HRMS(ES+) m/z Calcd for $C_{31}H_{30}Cl_2FN_3O_5$+H [(M+H): 586.1471; Found: 586.1473.

Example 36

Preparation of intermediate 5-(tert-butyl-dimethyl-silanyloxy)-3,3-dimethyl-pentanal

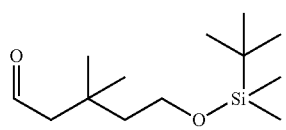

M.W. 244.45 C13H28O2Si

Step A

To the solution of 3,3-dimethylglutaric acid (Aldrich) (5.1 g, 32 mmol) in anhydrous tetrahydrofuran (100 mL) at 0° C. was added a solution of BH3.THF (1 M, 100 mL, 100 mmol). The reaction mixture was stirred at room temperature for 18 h. Aqueous HCl solution was added, and the mixture was extracted with ethyl acetate. The organic layer was separated, washed with saturated aqueous NaHCO3 solution, brine, dried over MgSO4, and concentrated. The residue was purified by chromatography (EtOAc) to give 3,3-dimethyl-pentane-1,5-diol as a colorless oil (1.5 g, 34%).

Step B

A mixture of 3,3-dimethyl-pentane-1,5-diol (1.5 g, 11 mmol) and imidazole (1.4 g, 20 mmol) in dichloromethane (50 mL) was added tert-butyldimethylchlorosilane (1.7 g, 11 mmol). The reaction mixture was stirred at room temperature for 2 h. Water was added. The organic layer was separated, the aqueous layer was then extracted with dichloromethane. The combined organic layers were washed with brine, dried over MgSO4, concentrated to give 5-(tert-butyl-dimethyl-silanyloxy)-3,3-dimethyl-pentan-1-ol as a colorless oil (2.7 g, 100%).

Step C

To a solution of oxalyl chloride (0.97 mL, 11 mmol) (Aldrich) in dichloromethane (20 mL) at −78° C. was added the solution of dimethyl sulfoxide (1.6 mL, 22 mmol) in dichloromethane (5 mL) dropwise. After 5 mins, the solution of 5-(tert-butyl-dimethyl-silanyloxy)-3,3-dimethyl-pentan-1-ol (2.5 g, 10 mmol) in dichloromethane (10 mL) was added dropwise. The reaction mixture was stirred at −78° C. for 15 min. Triethylamine (5 mL, 36 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO3, brine, dried over MgSO4, and concentrated to give 5-(tert-butyl-dimethyl-silanyloxy)-3,3-dimethyl-pentanal as a light yellow oil (Yield: 1.75 g, 71%).

Example 37

Preparation of intermediate E/Z-3-[5-(tert-butyl-dimethyl-silanyloxy)-3,3-dimethyl-pentylidene]-6-chloro-1,3-dihydro-indol-2-one

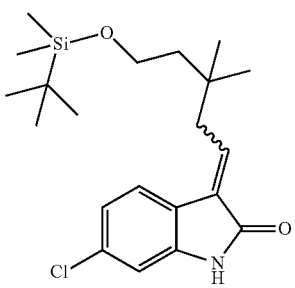

M.W.394.03 C21H32ClNO2Si

To the mixture of 6-chlorooxindole (3.3 g, 20 mmol) (Crescent) and 5-(tert-butyl-dimethyl-silanyloxy)-3,3-dimethyl-pentanal (6.5 g, 26.6 mmol) in methanol (150 mL) was added a methanolic solution (25%, Aldrich) of sodium methoxide (10 g, 46 mmol) dropwise. The reaction mixture was stirred at room temperature for 10 min. The solvent was removed, and the residue was partitioned between ethyl acetate and water. The organic layer was separated, dried over Na2SO4, and concentrated. The residue was purified by chromatography (25-33% EtOAc in hexanes) to give E/Z-3-[5-(tert-butyl-dimethyl-silanyloxy)-3,3-dimethyl-pentylidene]-6-chloro-1,3-dihydro-indol-2-one as a off white solid (Yield 3.6 g, 46%).

Example 38

Preparation of intermediate racemic 3-[5-(tert-butyl-dimethyl-silanyloxy)-3,3-dimethyl-1-nitromethyl-pentyl]-6-chloro-1,3-dihydro-indol-2-one

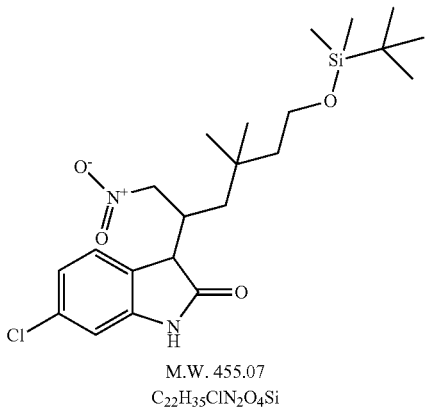

M.W. 455.07
C$_{22}$H$_{35}$ClN$_2$O$_4$Si

To a solution of nitromethane (Aldrich) (0.21 g, 3.5 mmol) in methanol (20 mL) was slowly added a methanolic solution (Aldrich, 25 wt. %) of sodium methoxide (0.74 g, 3.5 mmol). After the mixture was stirred at room temperature for 10 min, a solution of E/Z-3-[5-(tert-butyl-dimethyl-silanyloxy)-3,3-dimethyl-pentylidene]-6-chloro-1,3-dihydro-indol-2-one (0.68 g, 1.7 mmol) in methanol (10 mL) was added. The reaction mixture was stirred at room temperature for 2 h, then acetic acid (0.6 g, 10 mmol) was added. The mixture was concentrated to a small volume, then the residue was partitioned between ethyl acetate and water. The organic layer was separated, the aqueous layer was extracted with ethyl acetate. The organic layers were combined, washed with saturated aqueous NaHCO$_3$, brine, dried over MgSO$_4$, and concentrated. The residue was purified by chromatography (EtOAc:hexanes=1:10) to give the racemic 3-[5-(tert-butyl-dimethyl-silanyloxy)-3,3-dim ethyl-1-nitromethyl-pentyl]-6-chloro-1, 3-dihydro-indol-2-one as a white foam (0.5 g, 64%).

Example 39

Preparation of intermediate racemic 3-[1-aminomethyl-5-(tert-butyl-dimethyl-silanyloxy)-3,3-dimethyl-pentyl]-6-chloro-1,3-dihydro-indol-2-one

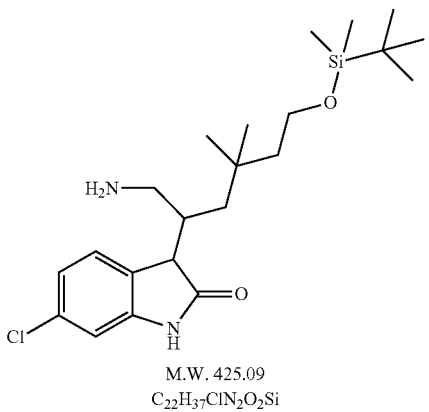

M.W. 425.09
C$_{22}$H$_{37}$ClN$_2$O$_2$Si

To a solution of racemic 3-[5-(tert-butyl-dimethyl-silanyloxy)-3,3-dimethyl-1-nitromethyl-pentyl]-6-chloro-1,3-dihydro-indol-2-one (0.5 g, 1.1 mmol) in methanol (20 mL) was added an aqueous solution (5 mL) of ammonium chloride (0.6 g, 11 mmol), followed by the addition of Zinc (Aldrich, activated) (0.7 g, 11 mmol). The reaction mixture was stirred at room temperature for 2 h. The mixture was filtered through a short pad of celite. The filtrate was concentrated to a small volume, then the residue was partitioned between ethyl acetate and water. The organic layer was separated, the aqueous layer was extracted with ethyl acetate. The organic layers were combined, washed with saturated aqueous NaHCO$_3$, brine, dried over MgSO$_4$, and concentrated to give racemic 3-[1-aminomethyl-5-(tert-butyl-dimethyl-silanyloxy)-3,3-dimethyl-pentyl]-6-chloro-1,3-dihydro-indol-2-one as a white foam (0.4 g, 86%)

Example 40

Preparation of intermediate rac-(2'S,3'S,4'S)-4'-[4-(tert-butyl-dimethyl-silanyloxy)-2,2-dimethyl-butyl]-6-chloro-2'-(3-chloro-2-fluoro-phenyl)-1H-spiro[indole-3,3'-pyrrolidin]-2-one

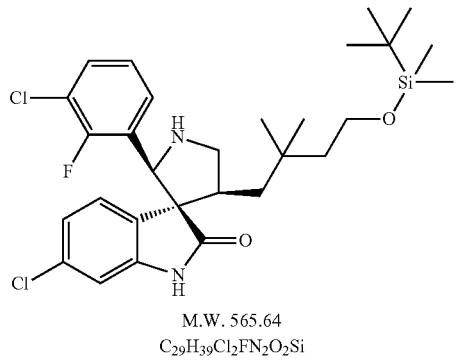

M.W. 565.64
C$_{29}$H$_{39}$Cl$_2$FN$_2$O$_2$Si

To a solution of racemic 3-[1-aminomethyl-5-(tert-butyl-dimethyl-silanyloxy)-3,3-dimethyl-pentyl]-6-chloro-1,3-dihydro-indol-2-one (1.5 g, 3.5 mmol) in toluene (30 mL) was added 3-chloro-2-fluoro-benzaldehyde (Oakwood) (0.56 g, 3.5 mmol) and a catalytic amount of p-toluenesulfonic acid monohydrate (67 mg, 0.35 mmol). The reaction mixture was heated at 130° C. for 2 h. The mixture was cooled to room temperature, then partitioned between ethyl acetate and aqueous NaHCO$_3$ solution. The organic layer was separated, and aqueous layer was extracted with ethyl acetate. The organic layers were combined, dried over MgSO$_4$ and concentrated. The residue was purified by chromatography (50-100% EtOAc in hexanes) to give rac-(2'S,3'S,4'S)-4'-[4-(tert-butyl-dimethyl-silanyloxy)-2,2-dimethyl-butyl]-6-chloro-2'-(3-chloro-2-fluoro-phenyl)-1H-spiro[indole-3,3'-pyrrolidin]-2-one as a white solid (0.12 g, 6%)

Example 41

Preparation of rac-(2'S,3'S,4'S)-6-chloro-2'-(3-chloro-2-fluoro-phenyl)-4'-(4-hydroxy-2,2-dimethyl-butyl)-2-oxo-1,2-dihydro-spiro[indole-3,3'-pyrrolidine]-1'-carboxylic acid ((S)-3,4-dihydroxy-butyl)-amide

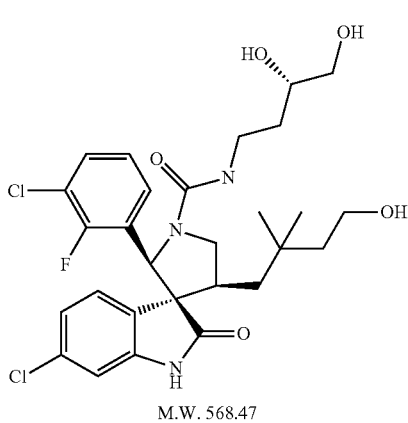

M.W. 568.47
$C_{28}H_{34}Cl_2FN_3O_5$

To a solution of rac-(2'S,3'S,4'S)-4'-[4-(tert-butyl-dimethyl-silanyloxy)-2,2-dimethyl-butyl]-6-chloro-2'-(3-chloro-2-fluoro-phenyl)-1H-spiro[indole-3,3'-pyrrolidin]-2-one prepared in Example 40 (70 mg, 0.12 mmol) in dichloromethane (5 mL) was added saturated aqueous $NaHCO_3$ solution (5 mL). The temperature of the mixture was lowered to 0° C., and a toluene solution (Aldrich, 20%) of phosgene (0.12 mL, 0.22 mmol) was added dropwise via a syringe. The reaction mixture was stirred at room temperature for 30 min, then diluted dichloromethane. The organic layer was separated, the aqueous layer was extracted with dichloromethane twice. The combined organic layers were washed with water, brine, dried over $MgSO_4$, and concentrated. The residue was dissolved into tetrahydrofuran (5 mL), and 2-((S)-2,2-dimethyl-[1,3]dioxolan-4-yl)-ethylamine prepared in Example 7 (36 mg, 0.25 mmol) was added. The reaction mixture was stirred at room temperature for 1 h. An aqueous HCl solution (1 N, 5 mL, 5 mmol) was added. The reaction mixture was stirred at room temperature for 1 h. The solvents were removed and the residue was partitioned between ethyl acetate and saturated aqueous $NaHCO_3$ solution. The organic layer was separated, and the aqueous layer was extracted with ethyl acetate. The organic layers were combined, washed with water, brine, dried over $MgSO_4$, and concentrated. The residue was purified by chromatography (15% MeOH in EtOAc) to give rac-(2'S,3'S,4'S)-6-chloro-2'-(3-chloro-2-fluoro-phenyl)-4'-(4-hydroxy-2,2-dimethyl-butyl)-2-oxo-1,2-dihydro-spiro[indole-3,3'-pyrrolidine]-1'-carboxylic acid ((S)-3,4-dihydroxy-butyl)-amide as a white solid (Yield 13 mg, 18%).

HRMS(ES$^+$) m/z Calcd for $C_{28}H_{34}Cl_2FN_3O_5$+H [(M+H)]: 554.1784; Found: 554.1785.

Example 42

Preparation of rac-4-{[(2'S,3'S,4'S)-6-chloro-2'43-chloro-2-fluoro-phenyl)-4'-(4-hydroxy-2,2-dimethyl-butyl)-2-oxo-1,2-dihydro-spiro[indole-3,3'-pyrrolidin]e-1'-carbonyl]-amino}-benzoic acid

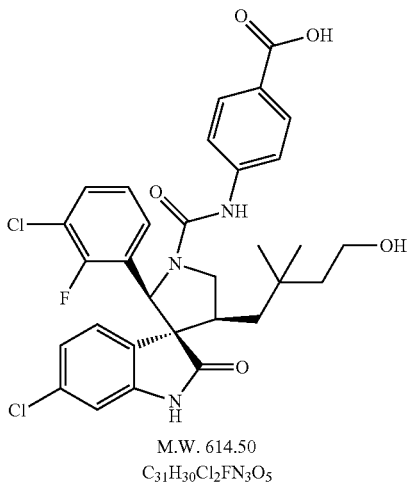

M.W. 614.50
$C_{31}H_{30}Cl_2FN_3O_5$

To a solution of rac-(2'S,3'S,4'S)-4'-[4-(tert-butyl-dimethyl-silanyloxy)-2,2-dimethyl-butyl]-6-chloro-2'-(3-chloro-2-fluoro-phenyl)-1H-spiro[indole-3,3'-pyrrolidin]-2-one prepared in Example 40 (50 mg, 0.09 mmol) in tetrahydrofuran (3 mL) was added 4-isocyanato-benzoic acid methyl ester (Aldrich) (16 mg, 0.09 mmol) and triethylamine (0.015 mL, 0.1 mmol). The reaction mixture was stirred at room temperature for 1 h. The solvent was removed. The residue was partitioned between ethyl acetate and water. The organic layer was separated, washed with water, brine, dried over $MgSO_4$, and concentrated. The residue was purified by chromatography (20% EtOAc in hexanes) to give rac-4-{[(2'S,3'S,4'S)-4'-[4-(tert-tutyl-dimethyl-silanyloxy)-2,2-dimethyl-butyl]-6-chloro-2'-(3-chloro-2-fluoro-phenyl)-2-oxo-1,2-dihydro-spiro[indole-3,3'-pyrrolidin]e-1'-carbonyl]-amino}-benzoic acid methyl ester as a light yellow solid. The light yellow solid was dissolved into tetrahydrofuran (5 mL), and an aqueous solution (1 N) of NaOH (6 mL, 6 mmol) and methanol (2 mL) were added. The reaction mixture was stirred at room temperature for 20 h, then heated at 100° C. for 3 h. The mixture was cooled to room temperature, and acidified to "pH" 1 by diluted aqueous HCl solution. The mixture was stirred at room temperature for 0.5 h. then concentrated. The residue was partitioned between ethyl acetate and water. The organic layer was separated, and the aqueous layer was extracted with ethyl acetate. The organic layers were combined, washed with water, brine, dried over $MgSO_4$, and concentrated. The residue was purified by chromatography (7% MeOH in EtOAc) to give rac-4{[(2'S,3'S,4'S)-6-chloro-2'-(3-chloro-2-fluoro-phenyl)-4'-(4-hydroxy-2,2-dimethyl-butyl)-2-oxo-1,2-dihydro-spiro[indole-3,3'-pyrrolidin]e-1'-carbonyl]-amino}-benzoic acid as a light yellow solid (Yield 13 mg, 24%).

HRMS(ES$^+$) m/z Calcd for $C_{31}H_{30}Cl_2FN_3O_5$+H [(M+H): 586.1471; Found: 586.1473.

Example 43

Preparation of rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-piperidine-1-carboxylic acid tert-butyl ester

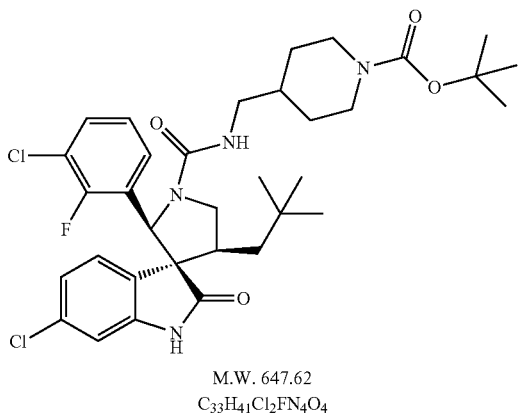

M.W. 647.62
$C_{33}H_{41}Cl_2FN_4O_4$

In a manner similar to the method described in Example 9, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride prepared in Example 8 (0.32 g, 0.66 mmol) was reacted with 4-aminomethyl-piperidine-1-carboxylic acid tert-butyl ester (Aldrich) (0.17 g, 0.79 mmol) and triethylamine to give rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-piperidine-1-carboxylic acid tert-butyl ester as a white solid (Yield, 80 mg, 18%).

HRMS(ES$^+$) m/z Calcd for $C_{33}H_{41}Cl_2FN_4O_4$+H [(M+H)]: 554.1784; Found: 554.1785.

Example 44

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylmethyl)-amide trifluoroacetic acid

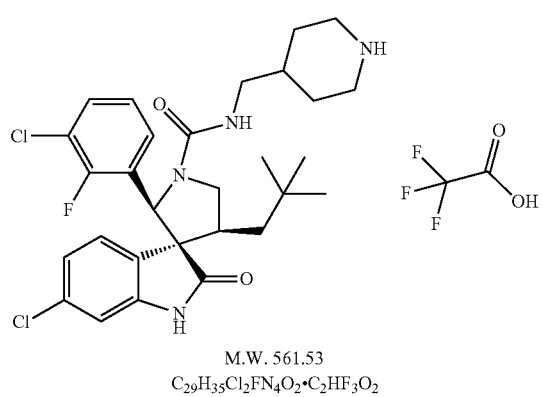

M.W. 561.53
$C_{29}H_{35}Cl_2FN_4O_2 \cdot C_2HF_3O_2$

In a manner similar to the method described in Example 25, rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-piperidine-1-carboxylic acid tert-butyl ester (70 mg, 0.1 mmol) was reacted with trifluoroacetic acid (2 mL) in dichloromethane (2 mL) to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylmethyl)-amide trifluoroacetic acid as a white solid (Yield, 68 mg, 96%).

HRMS(ES$^+$) m/z Calcd for $C_{29}H_{35}Cl_2FN_4O_2$+H [(M+H): 586.1471; Found: 586.1473.

Example 45

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide

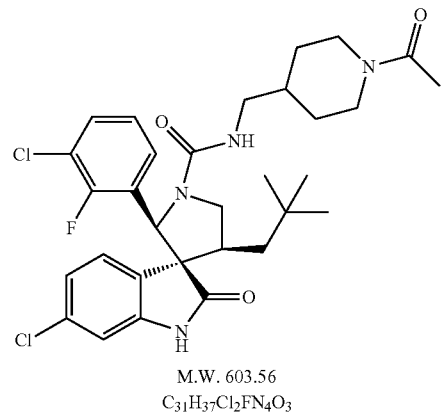

M.W. 603.56
$C_{31}H_{37}Cl_2FN_4O_3$

In a manner similar to the method described in Example 26, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylmethyl)-amide trifluoroacetic acid (25 mg, 0.04 mmol) was reacted with triethylamine and acetyl chloride (3.2 mg, 0.04 mmol) in tetrahydrofuran to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide as a white solid (Yield, 17 mg, 77%).

HRMS(ES$^+$) m/z Calcd for $C_{31}H_{37}Cl_2FN_4O_3$+H [(M+H): 586.1471; Found: 586.1473.

Example 46

Preparation of chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide

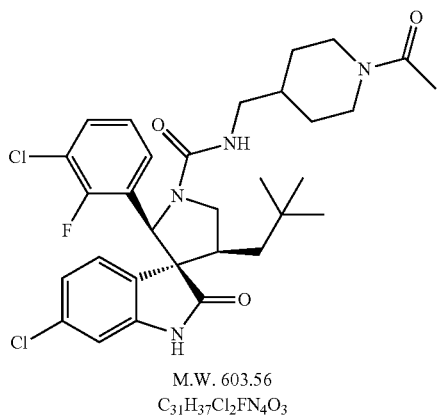

M.W. 603.56
$C_{31}H_{37}Cl_2FN_4O_3$

Rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide (100 mg) was separated by chiral SFC chromatography to provide chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide as a white solid (43 mg, 43%) and chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide as a white solid (41 mg, 41%).

Example 47

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-ylmethyl)-amide

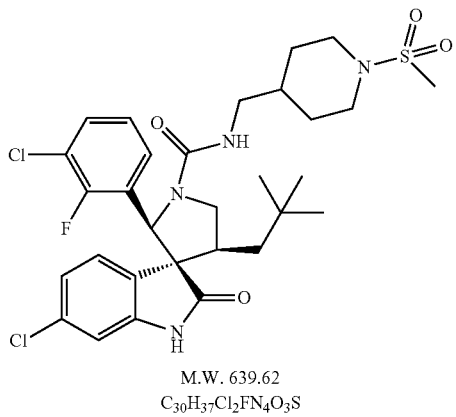

M.W. 639.62
$C_{30}H_{37}Cl_2FN_4O_3S$

In a manner similar to the method described in Example 27, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylmethyl)-amide trifluoroacetic acid prepared in Example 44 (35 mg, 0.05 mmol) was reacted with triethylamine and methanesulfonyl chloride (6.5 mg, 0.06 mmol) in dichloromethane to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-ylmethyl)-amide as a white solid (Yield, 13 mg, 39%).

HRMS(ES+) m/z Calcd for $C_{30}H_{37}Cl_2FN_4O_3S+H$ [(M+H):586.1471; Found: 586.1473.

Example 48

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-benzyl ester

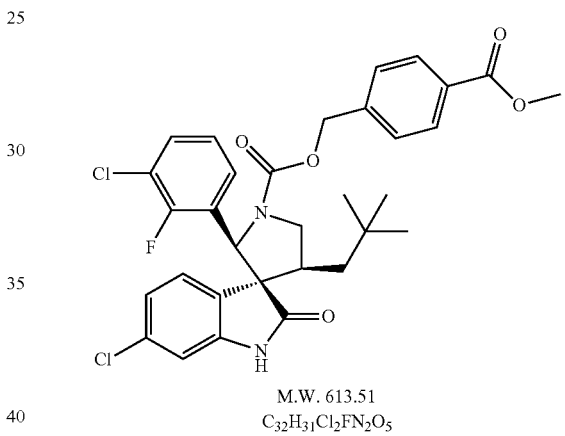

M.W. 613.51
$C_{32}H_{31}Cl_2FN_2O_5$

To a solution of methyl 4-(hydroxymethyl)benzoate (20 mg, 0.12 mmol) in tetrahydrofuran (3 mL) was added a toluene solution (Aldrich, 20%) of phosgene (0.25 mL, 0.48 mmol) dropwise via a syringe. The reaction mixture was stirred at room temperature for 1 h, then the solvents were removed. The residue was dissolved into tetrahydrofuran (3 mL), and rac-(2'S,3'S,4'S)-6-chloro-2'-(3-chloro-2-fluoro-phenyl)-4'-(2,2-dimethyl-propyl)-1H-spiro[indole-3,3'-pyrrolidin]-2-one prepared in Example 6 (56 mg, 0.13 mmol) and triethylamine (0.04 mL, 0.29 mmol) were added sequentially. The reaction mixture was stirred at room temperature for 18 h. The solvents were removed, and the residue was partitioned between ethyl acetate and water. The organic layer was separated, and the aqueous layer was extracted with ethyl acetate. The organic layers were combined, washed with water, brine, dried over MgSO₄, and concentrated. The residue was purified by chromatography (35% EtOAc in hexanes) to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-benzyl ester as a white solid (Yield 55 mg, 68%).

HRMS(ES+) m/z Calcd for $C_{32}H_{31}Cl_2FN_2O_5+H$ [(M+H)]: 554.1784; Found: 554.1785.

Example 49

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carboxy-benzyl ester

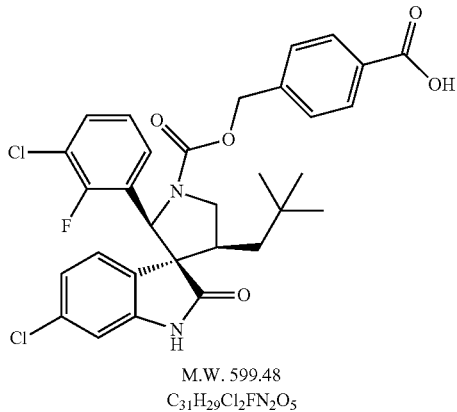

M.W. 599.48
$C_{31}H_{29}Cl_2FN_2O_5$

In a manner similar to the method described in Example 13, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-benzyl ester (50 mg, 0.08 mmol) was heated with aqueous LiOH (19 mg, 0.8 mmol) in tetrahydrofuran (3 mL), water (3 mL), and methanol (1 mL) at room temperature for 18 h to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carboxy-benzyl ester as a white solid (Yield, 35 mg, 71%).

HRMS(ES$^+$) m/z Calcd for $C_{31}H_{29}Cl_2FN_2O_5$+H [(M+H): 586.1471; Found: 586.1473.

Example 50

Preparation of rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-ethyl)-piperidine-1-carboxylic acid tert-butyl ester

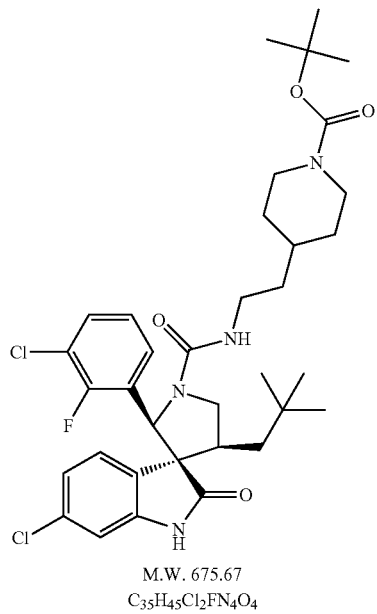

M.W. 675.67
$C_{35}H_{45}Cl_2FN_4O_4$

In a manner similar to the method described in Example 9, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride prepared in Example 8 (0.6 g, 1.3 mmol) was reacted with 4-aminoethyl-piperidine-1-carboxylic acid tert-butyl ester (0.57 g, 2.5 mmol) and triethylamine to give rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-ethyl)-piperidine-1-carboxylic acid tert-butyl ester as a white solid (Yield, 80 mg, 9%).

HRMS(ES$^+$) m/z Calcd for $C_{35}H_{45}Cl_2FN_4O_4$+H [(M+H)]: 554.1784; Found: 554.1785.

Example 51

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylethyl)-amide trifluoroacetic acid

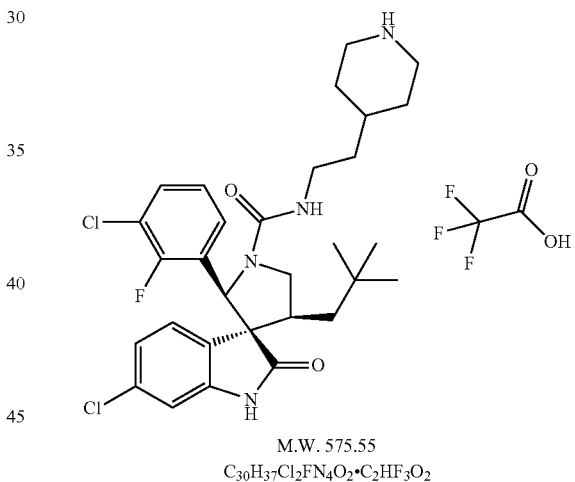

M.W. 575.55
$C_{30}H_{37}Cl_2FN_4O_2 \cdot C_2HF_3O_2$

In a manner similar to the method described in Example 25, rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-ethyl)-piperidine-1-carboxylic acid tert-butyl ester (74 mg, 0.1 mmol) was reacted with trifluoroacetic acid (2 mL) in dichloromethane (2 mL) to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylethyl)-amide trifluoroacetic acid as a white solid (Yield, 75 mg, 99%).

HRMS(ES$^+$) m/z Calcd for $C_{30}H_{37}Cl_2FN_4O_2$+H [(M+H): 586.1471; Found: 586.1473.

Example 52

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-ylethyl)-amide

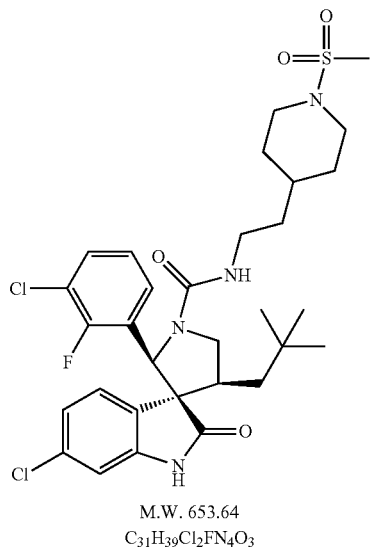

M.W. 653.64
$C_{31}H_{39}Cl_2FN_4O_3$

In a manner similar to the method described in Example 27, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylethyl)-amide trifluoroacetic acid prepared in Example 51 (30 mg, 0.04 mmol) was reacted with triethylamine and methanesulfonyl chloride (5.5 mg, 0.05 mmol) in dichloromethane to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-ylethyl)-amide as a white solid (Yield, 27 mg, 959%).

HRMS(ES$^+$) m/z Calcd for $C_{31}H_{39}Cl_2FN_4O_3$+H [(M+H): 586.1471; Found: 586.1473.

Example 53

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylethyl)-amide

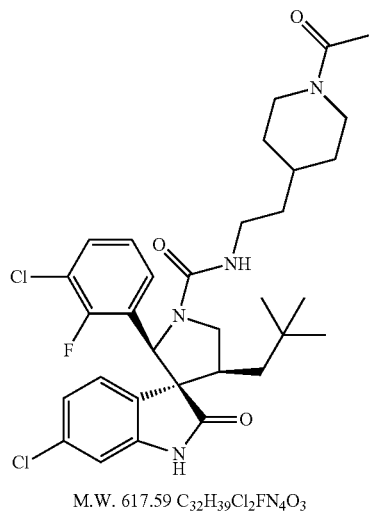

M.W. 617.59 $C_{32}H_{39}Cl_2FN_4O_3$

In a manner similar to the method described in Example 26, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylethyl)-amide trifluoroacetic acid prepared in Example 51 (30 mg, 0.04 mmol) was reacted with triethylamine and acetyl chloride (3.8 mg, 0.05 mmol) in tetrahydrofuran to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylethyl)-amide as a white solid (Yield, 23 mg, 86%).

HRMS(ES$^+$) m/z Calcd for $C_{32}H_{39}Cl_2FN_4O_3$+H [(M+H): 586.1471; Found: 586.1473.

Example 54

Preparation of rac-(2'S,3'S,4'S)-6-chloro-2'-(3-chloro-2-fluoro-phenyl)-4'-(2,2-dimethyl-propyl)-1'-[4-(3-methanesulfonyl-propyl)-piperazine-1-carbonyl]-1H-spiro[indole-3,3'-pyrrolidin]-2-one

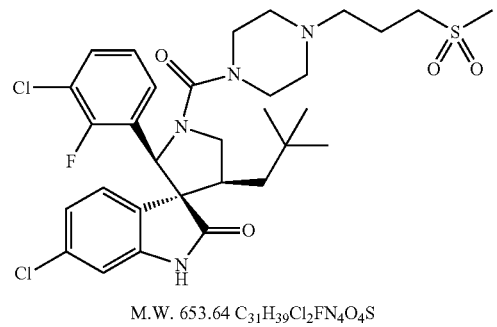

M.W. 653.64 $C_{31}H_{39}Cl_2FN_4O_4S$

In a manner similar to the method described in Example 9, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride prepared in Example 8 (53 mg, 0.11 mmol) was reacted with 1-(3-methanesulfonyl-propyl)-piperazine (34 mg, 0.14 mmol) and triethylamine to give rac-(2'S,3'S,4'S)-6-chloro-2'-(3-chloro-2-fluoro-phenyl)-4'-(2,2-dimethyl-propyl)-1'-[4-(3-methanesulfonyl-propyl)-piperazine-1-carbonyl]-1H-spiro[indole-3,3'-pyrrolidin]-2-one as a white solid (Yield, 61 mg, 79%).

HRMS(ES$^+$) m/z Calcd for $C_{31}H_{39}Cl_2FN_4O_4S$+H [(M+H)]: 554.1784. Found: 554.1785.

Example 55

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1H-pyrazol-3-ylmethyl)-amide

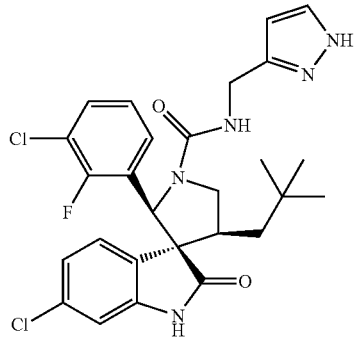

M.W. 544.46 $C_{27}H_{28}Cl_2FN_5O_2$

In a manner similar to the method described in Example 9, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride prepared in Example 8 (57 mg, 0.12 mmol) was reacted with C-(1H-pyrazol-3-yl)-methylamine (Oakwood) (20 mg, 0.18 mmol) and triethylamine to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-F-carboxylic acid (1H-pyrazol-3-ylmethyl)-amide as a white solid (Yield, 23 mg, 36%).

HRMS(ES$^+$) m/z Calcd for $C_{27}H_{28}Cl_2FN_5O_2$+H [(M+H)]: 554.1784; Found: 554.1785.

Example 56

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methyl-1H-pyrazol-3-ylmethyl)-amide

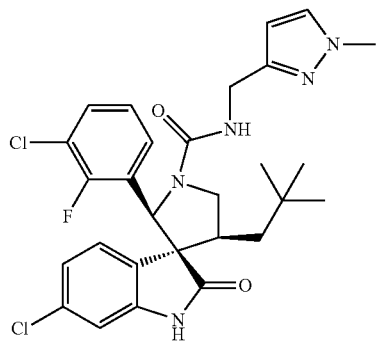

M.W. 558.48 $C_{28}H_{30}Cl_2FN_5O_2$

In a manner similar to the method described in Example 9, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride prepared in Example 8 (57 mg, 0.12 mmol) was reacted with (1-methyl-1H-pyrazol-3-yl)methylamine (Oakwood) (20 mg, 0.18 mmol) and triethylamine to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methyl-1H-pyrazol-3-ylmethyl)-amide as a white solid (Yield, 18 mg, 27%).

HRMS(ES$^+$) m/z Calcd for $C_{28}H_{30}Cl_2FN_5O_2$+H [(M+H)]: 554.1784; Found: 554.1785.

Example 57

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1,3-dimethyl-1H-pyrazol-4-ylmethyl)-amide

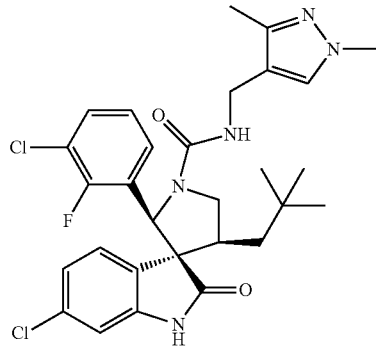

M.W. 572.51 $C_{29}H_{32}Cl_2FN_5O_2$

In a manner similar to the method described in Example 9, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonylchloride prepared in Example 8 (57 mg, 0.12 mmol) was reacted with C-(1,3-dimethyl-1H-pyrazol-4-yl)methylamine (Oakwood) (22 mg, 0.18 mmol) and triethylamine to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1,3-dimethyl-1H-pyrazol-4-ylmethyl)-amide as a white solid (Yield, 19 mg, 28%).

HRMS(ES$^+$) m/z Calcd for $C_{29}H_{32}Cl_2FN_5O_2$+H [(M+H)]: 554.1784; Found: 554.1785.

Example 58

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (4-nitro-phenyl)-amide

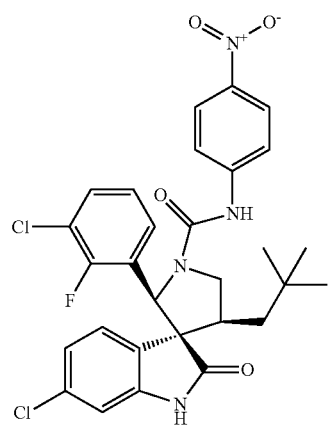

M.W. 585.46 $C_{29}H_{27}Cl_2FN_4O_4$

In a manner similar to the method described in Example 11, rac-(2'S,3'S,4'S)-6-chloro-2'-(3-chloro-2-fluoro-phenyl)-4'-(2,2-dimethyl-propyl)-1H-spiro[indole-3,3'-pyrrolidin]-2-one prepared in Example 6 (0.1 g, 0.24 mmol) was reacted with 4-nirophenyl isocyanate (Aldrich) (39 mg, 0.24 mmol) and triethylamine in tetrahydrofuran to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (4-nitro-phenyl)-amide as a yellow solid (Yield, 0.11 g, 80%).

HRMS(ES$^+$) m/z Calcd for $C_{29}H_{27}Cl_2FN_4O_4$+H [(M+H)]: 554.1784; Found: 554.1785.

Example 59

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-phenyl ester

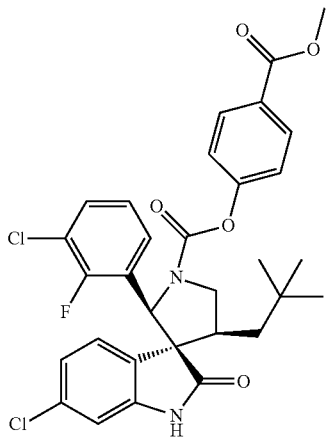

M.W. 599.48 $C_{31}H_{29}Cl_2FN_2O_5$

To a solution of methyl 4-hydroxybenzoate (Aldrich) (20 mg, 0.13 mmol) in N,N-dimethylforamide (3 mL) was added NaH (60%, 7.8 mg, 0.2 mmol). The reaction mixture was stirred at room temperature for 10 min, then rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carbonyl chloride prepared in Example 8 (56 mg, 0.13 mmol) was added. The reaction mixture was stirred at room temperature for 3 h. Water was added. The mixture was partitioned between ethyl acetate and water. The organic layer was separated, and the aqueous layer was extracted with ethyl acetate. The organic layers were combined, washed with water, brine, dried over MgSO$_4$, and concentrated. The residue was triturated with dichloromethane and hexanes to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-phenyl ester as a white solid (Yield 14 mg, 18%).

HRMS(ES$^+$) m/z Calcd for $C_{31}H_{29}Cl_2FN_2O_5$+H [(M+H)]: 554.1784; Found: 554.1785.

Example 59

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carboxy-phenyl ester

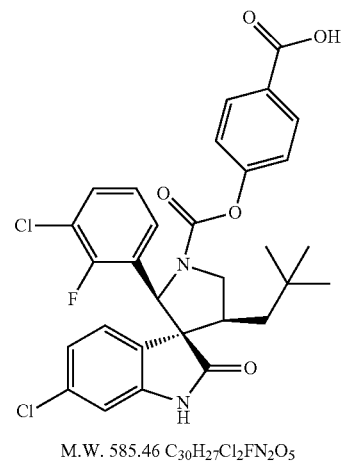

M.W. 585.46 $C_{30}H_{27}Cl_2FN_2O_5$

In a manner similar to the method described in Example 13, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-phenyl ester (10 mg, 0.02 mmol) was heated with aqueous LiOH (4 mg, 0.2 mmol) in tetrahydrofuran (3 mL), water (3 mL), and methanol (1 mL) at room temperature for 18 h to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carboxy-phenyl ester as a white solid (Yield, 8 mg, 82%).

HRMS(ES$^+$) m/z Calcd for $C_{30}H_{27}Cl_2FN_2O_5$+H [(M+H): 586.1471; Found: 586.1473.

Example 60

Preparation of rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (4-carbamoyl-phenyl)-amide

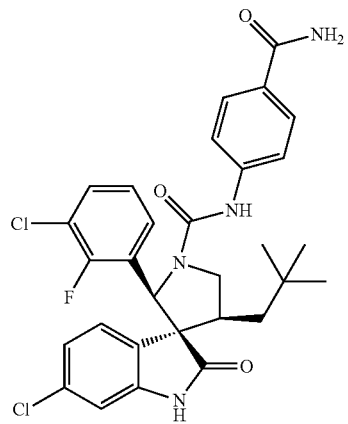

M.W. 583.49 $C_{30}H_{29}Cl_2FN_4O_3$

To a solution of rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid prepared in Example 13 (0.19 g, 0.32 mmol) in N,N-dimethylformamide (5 mL) was added NH$_4$Cl (0.18 g, 3.2 mmol), EDCI (75 mg, 0.39 mmol), HOBT (53 mg, 0.39 mmol) and NEt$_3$ (0.1 mL, 0.72 mmol). The reaction mixture was heated at 85° C. for 1 h. The mixture was cooled to room temperature, and partitioned between ethyl acetate and water. The organic layer was separated, and the aqueous layer was extracted with ethyl acetate. The organic layers were combined, washed with water, brine, dried over MgSO$_4$, and concentrated. The residue was triturated with dichloromethane and hexanes to give rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (4-carbamoyl-phenyl)-amide as a white solid (0.17 g, 87%). FIRMS (ES$^-$) m/z Calcd for C$_{30}$H$_{29}$Cl$_2$FN$_4$O$_3$+H [(M+H)$^+$]: 575.1423. Found: 575.1425.

Example 61

Preparation of chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carbamoyl-benzylamide

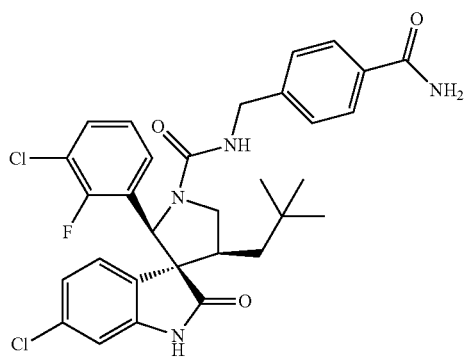

M.W. 597.52 C$_{31}$H$_{31}$Cl$_2$FN$_4$O$_3$

To a solution of chiral 4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid prepared in Example 23 (70 mg, 0.12 mmol) in N,N-dimethylformamide (2 mL) was added NH$_4$Cl (62 mg, 1.2 mmol), EDCI (45 mg, 0.23 mmol), HOBT (32 mg, 0.23 mmol) and NEt$_3$ (0.03 mL, 0.23 mmol). The reaction mixture was heated at 80° C. for 1 h. The mixture was cooled to room temperature, and partitioned between ethyl acetate and water. The organic layer was separated, and the aqueous layer was extracted with ethyl acetate. The organic layers were combined, washed with water, brine, dried over MgSO$_4$, and concentrated. The residue was purified by chromatography (25-100% EtOAc in hexanes) to give chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carbamoyl-benzylamide as a off white solid (45 mg, 64%).

HRMS(ES$^+$) m/z Calcd for C$_{31}$H$_{31}$Cl$_2$FN$_4$O$_3$+H [(M+H)$^+$]: 575.1423; Found: 575.1425.

Example 62

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co. Activity data for some of the Example compounds expressed as IC$_{50}$:bsa:0.02% are as follows:

| Example Number | IC$_{50}$: bsa: 0.02% |
|---|---|
| 6 | 0.773 |
| 12 | 0.581 |
| 28 | 0.133 |
| 33 | 0.725 |
| 49 | 0.178 |

What is claimed:
1. A compound of the formula

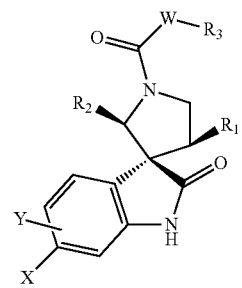

wherein
X is selected from the group consisting of F, Cl and Br;
Y is a mono substituting group selected from H or F;
R$_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_2$ is selected from the group consisting of aryl, substituted aryl, heteroaryl and substituted heteroaryl;

W is NH, O or none;

$R_3$ is selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR'R" and $(CH_2)_n$—SO$_2$NR'R";

n is 0, 1, 2 or 3;

R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle or substituted heterocycle and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle;

and enantiomers and the pharmaceutically acceptable salts thereof.

2. A compound of formula II

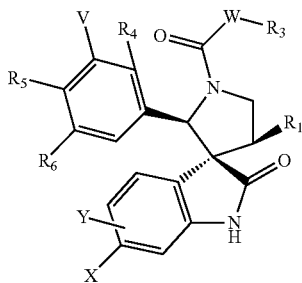

wherein,

X is selected from the group consisting of F, Cl and Br;

Y is a mono substituting group selected from H or F;

V is selected from the group consisting of F, Cl and Br;

$R_4$, $R_5$, $R_6$ is selected from H or F with the proviso that at least two of $R_3$, $R_4$, $R_5$ are hydrogen;

$R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

W is NH, O or none;

$R_3$ is selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR'R" and $(CH_2)_n$—SO$_2$NR'R";

n is 0, 1, 2 or 3;

R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle or substituted heterocycle and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle;

and enantiomers and the pharmaceutically acceptable salts thereof.

3. A compound of formula III

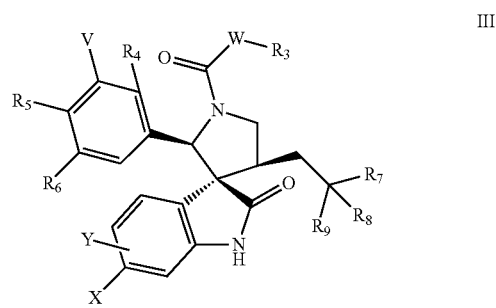

wherein,

X is selected from the group consisting of F, Cl and Br;

Y is a mono substituting group selected from H or F;

V is selected from the group consisting of F, Cl and Br;

$R_4$, $R_5$, $R_6$ is selected from H or F with the proviso that at least two of $R_3$, $R_4$, $R_5$ are hydrogen;

$R_7$, $R_8$ are both methyl, or linked to form a cyclopropyl, cyclobutyl, cyclopentyl or cyclohexyl group;

$R_9$ is $(CH_2)_q$—$R_{10}$;

$R_{10}$ is selected from hydrogen, hydroxyl, lower alkyl, lower alkoxy, lower cycloalkenyl, substituted cycloalkenyl, lower cycloalkyl, substituted cycloalkyl, aryl, substituted aryl, hetereoaryl, substituted heteroaryl, hetereocycle or substituted heterocycle;

q is 0, 1 or 2;

W is NH, O or none;

$R_3$ is selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR'R" and $(CH_2)_n$—SO$_2$NR'R";

n is 0, 1, 2 or 3;

R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle or substituted heterocycle and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle;

and enantiomers and the pharmaceutically acceptable salts thereof.

4. A compound of formula IV

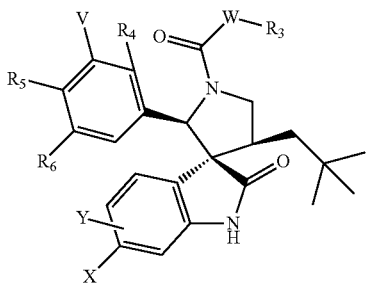

wherein,
X is selected from the group consisting of F, Cl and Br;
Y is a mono substituting group selected from H or F;
V is selected from the group consisting of F, Cl and Br;
$R_4$, $R_5$, $R_6$ is selected from H or F with the proviso that at least two of $R_3$, $R_4$, $R_5$ are hydrogen;
W is NH or O;
$R_3$ is selected from the group consisting of $(CH_2)_n$—R';
n is 0 or 1;
R' is selected from the group consisting of aryl, substituted aryl, heteroaryl and substituted heteroaryl;
and the pharmaceutically acceptable salts thereof.

5. A compound of claim 1 selected from the group consisting of
rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide,
chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide,
rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid ethyl ester,
rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid methyl ester,
rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid,
chiral 4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-benzoic acid,
rac-(2'R,3'S,4'S)-6-chloro-2'-(3-chloro-phenyl)-4'-(2,2-dimethyl-propyl)-2-oxo-1,2-dihydro-spiro[indole-3,3'-pyrrolidine]-1'-carboxylic acid ((S)-3,4-dihydroxy-butyl)-amide,
rac-4-{[(2'R,3'S,4'S)-6-chloro-2'-(3-chloro-phenyl)-4'-(2,2-dimethyl-propyl)-2-oxo-1,2-dihydro-spiro[indole-3,3'-pyrrolidin]e-1'-carbonyl]-amino}-benzoic acid methyl ester,
rac-4-{[(2'R,3'S,4'S)-6-chloro-2'-(3-chloro-phenyl)-4'-(2,2-dimethyl-propyl)-2-oxo-1,2-dihydro-spiro[indole-3,3'-pyrrolidin]e-1'-carbonyl]-amino}-benzoic acid,
rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid methyl ester and
rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid.

6. A compound of claim 1 selected from the group consisting of
chiral 4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-benzoic acid,
rac-4-{[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-piperidine-1-carboxylic acid tert-butyl ester,
rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid piperidin-4-ylamide trifluoroacetic acid,
rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-yl)-amide,
rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide,
chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-yl)-amide,
rac-(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidine]-1'-carboxylic acid ((S)-3,4-dihydroxy-butyl)-amide,
rac-4-({[(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidin]e-1'-carbonyl]-amino}-methyl)-benzoic acid methyl ester,
rac-4-({[(2'S,3'S,4'S)-6-chloro-2'-(3-chloro-2-fluoro-phenyl)-4'-(3-hydroxy-2,2-dimethyl-propyl)-2-oxo-1,2-dihydro-spiro[indole-3,3'-pyrrolidin]e-1'-carbonyl]-amino}-methyl)-benzoic acid,
rac-(2'S,3'S,4'S)-6-chloro-2'-(3-chloro-2-fluoro-phenyl)-4'-(4-hydroxy-2,2-dimethyl-butyl)-2-oxo-1,2-dihydro-spiro[indole-3,3'-pyrrolidine]-1'-carboxylic acid ((S)-3,4-dihydroxy-butyl)-amide and
rac-4-{[(2'S,3'S,4'S)-6-chloro-2'-(3-chloro-2-fluoro-phenyl)-4'-(4-hydroxy-2,2-dimethyl-butyl)-2-oxo-1,2-dihydro-spiro[indole-3,3'-pyrrolidin]e-1'-carbonyl]-amino}-benzoic acid.

7. A compound of claim 1 selected from the group consisting of
rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-methyl)-piperidine-1-carboxylic acid tert-butyl ester,
rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylmethyl)-amide trifluoroacetic acid,
rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide, chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-benzyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carboxy-benzyl ester, rac-4-({[(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidin]e-1'-carbonyl]-amino}-ethyl)-piperidine-1-carboxylic acid tert-butyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (piperidin-4-ylethyl)-amide trifluoroacetic acid, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methanesulfonyl-piperidin-4-ylethyl)-amide and rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-acetyl-piperidin-4-ylethyl)-amide.

8. A compound of claim 1 selected from the group consisting of rac-(2'S,3'S,4'S)-6-chloro-2'-(3-chloro-2-fluoro-phenyl)-4'-(2,2-dimethyl-propyl)-1'-[4-(3-methanesulfonyl-propyl)-piperazine-1-carbonyl]-1H-spiro[indole-3,3'-pyrrolidin]-2-one, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1H-pyrazol-3-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1-methyl-1H-pyrazol-3-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (1,3-dimethyl-1H-pyrazol-4-ylmethyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (4-nitro-phenyl)-amide, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-methoxycarbonyl-phenyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carboxy-phenyl ester, rac-(2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid (4-carbamoyl-phenyl)-amide and chiral (2'S,3'S,4'S)-6-chloro-2'-(3-chloro-2-fluoro-phenyl)-4'-(2,2-dimethyl-propyl)-2-oxo-1,2-dihydro-spiro[indole-3,3'-pyrrolidine]-1'-carboxylic acid 4-carbamoyl-benzylamide.

9. A pharmaceutical formulation comprising a compound of the formula

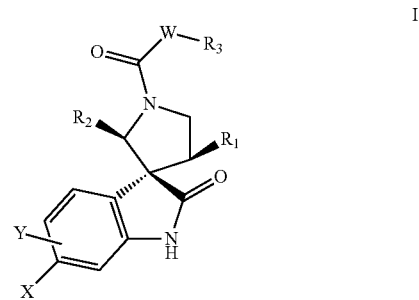

wherein

X is selected from the group consisting of F, Cl and Br;

Y is a mono substituting group selected from H or F;

$R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_2$ is selected from the group consisting of aryl, substituted aryl, heteroaryl and substituted heteroaryl;

W is NH, O or none;

$R_3$ is selected from the group consisting of $(CH_2)_n$—R', $(CH_2)_n$—NR'R", $(CH_2)_n$—NR'COR", $(CH_2)_n$—NR'SO_2R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO_2R', $(CH_2)_n$—COR', $(CH_2)_n$—SO_3H, $(CH_2)_n$—SONR'R" and $(CH_2)_n$—SO_2NR'R";

n is 0, 1, 2 or 3;

R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle or substituted heterocycle and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle;

and enantiomers and the pharmaceutically acceptable salts thereof together with a pharmaceutically acceptable excipient or carrier.

* * * * *